United States Patent
Twomey et al.

(10) Patent No.: US 8,603,134 B2
(45) Date of Patent: Dec. 10, 2013

(54) LATCH MECHANISM FOR SURGICAL INSTRUMENTS

(75) Inventors: John R. Twomey, Superior, CO (US); Russell Hempstead, Lafayette, CO (US); Keir Hart, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 252 days.

(21) Appl. No.: 13/007,182

(22) Filed: Jan. 14, 2011

(65) Prior Publication Data

US 2012/0184988 A1 Jul. 19, 2012

(51) Int. Cl.
*A61B 17/00* (2006.01)

(52) U.S. Cl.
USPC ............................. 606/205; 606/208; 66/206

(58) Field of Classification Search
None
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,211,655 A | 5/1993 | Hasson |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,381,788 A * | 1/1995 | Matula et al. .............. 600/214 |
| D358,887 S | 5/1995 | Feinberg |
| 5,564,615 A * | 10/1996 | Bishop et al. .............. 227/175.1 |
| D384,413 S | 9/1997 | Zlock et al. |
| D402,028 S | 12/1998 | Grimm et al. |
| 5,893,863 A | 4/1999 | Yoon |
| 5,935,126 A | 8/1999 | Riza |
| D416,089 S | 11/1999 | Barton et al. |
| D424,694 S | 5/2000 | Tetzlaff et al. |
| D425,201 S | 5/2000 | Tetzlaff et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler.

(Continued)

*Primary Examiner* — Katherine Dowe
*Assistant Examiner* — Sidharth Kapoor

(57) ABSTRACT

A surgical instrument includes a pair of jaw members moveable between a spaced-apart and an approximated position. A drive bar is translatable between a distal and a proximal position for moving the jaw members between the spaced-apart and approximated positions. A lever is moveable between an initial position and an actuated position for translating the drive bar between the distal and proximal positions. A sleeve disposed about the drive bar includes an annular track having a substantially radial segment(s) and a substantially longitudinal segment(s). A collar interdisposed between the sleeve and the drive bar includes a stop member(s) extending radially outwardly therefrom. The stop member(s) is engaged within the track and is translatable from a first position, wherein the stop member is positioned within the longitudinal segment, to a second position, wherein the stop member is engaged within the radial segment, to lock the lever in the actuated position.

4 Claims, 13 Drawing Sheets

(56) References Cited

U.S. PATENT DOCUMENTS

| | | | |
|---|---|---|---|
| 6,179,834 | B1 | 1/2001 | Buysse et al. |
| D449,886 | S | 10/2001 | Tetzlaff et al. |
| D454,951 | S | 3/2002 | Bon |
| D457,958 | S | 5/2002 | Dycus et al. |
| D457,959 | S | 5/2002 | Tetzlaff et al. |
| D465,281 | S | 11/2002 | Lang |
| D466,209 | S | 11/2002 | Bon |
| D493,888 | S | 8/2004 | Reschke |
| D496,997 | S | 10/2004 | Dycus et al. |
| D499,181 | S | 11/2004 | Dycus et al. |
| D502,994 | S | 3/2005 | Blake, III |
| D509,297 | S | 9/2005 | Wells |
| D525,361 | S | 7/2006 | Hushka |
| D531,311 | S | 10/2006 | Guerra et al. |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| D541,418 | S | 4/2007 | Schechter et al. |
| D541,611 | S | 5/2007 | Aglassinger |
| D541,938 | S | 5/2007 | Kerr et al |
| D545,432 | S | 6/2007 | Watanabe |
| D547,154 | S | 7/2007 | Lee |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| D582,038 | S | 12/2008 | Swoyer et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| D627,462 | S | 11/2010 | Kingsley |
| D628,289 | S | 11/2010 | Romero |
| D628,290 | S | 11/2010 | Romero |
| D630,324 | S | 1/2011 | Reschke |
| 2007/0233019 | A1* | 10/2007 | Forsell ............ 604/288.03 |
| 2011/0054483 | A1* | 3/2011 | Howlett et al. ............ 606/96 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/576,380, filed Oct. 9, 2009, Wayne Siebrecht.
U.S. Appl. No. 12/607,191, filed Oct. 28, 2009, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.

(56) References Cited

OTHER PUBLICATIONS

U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, GyneCologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques", OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

(56) References Cited

OTHER PUBLICATIONS

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

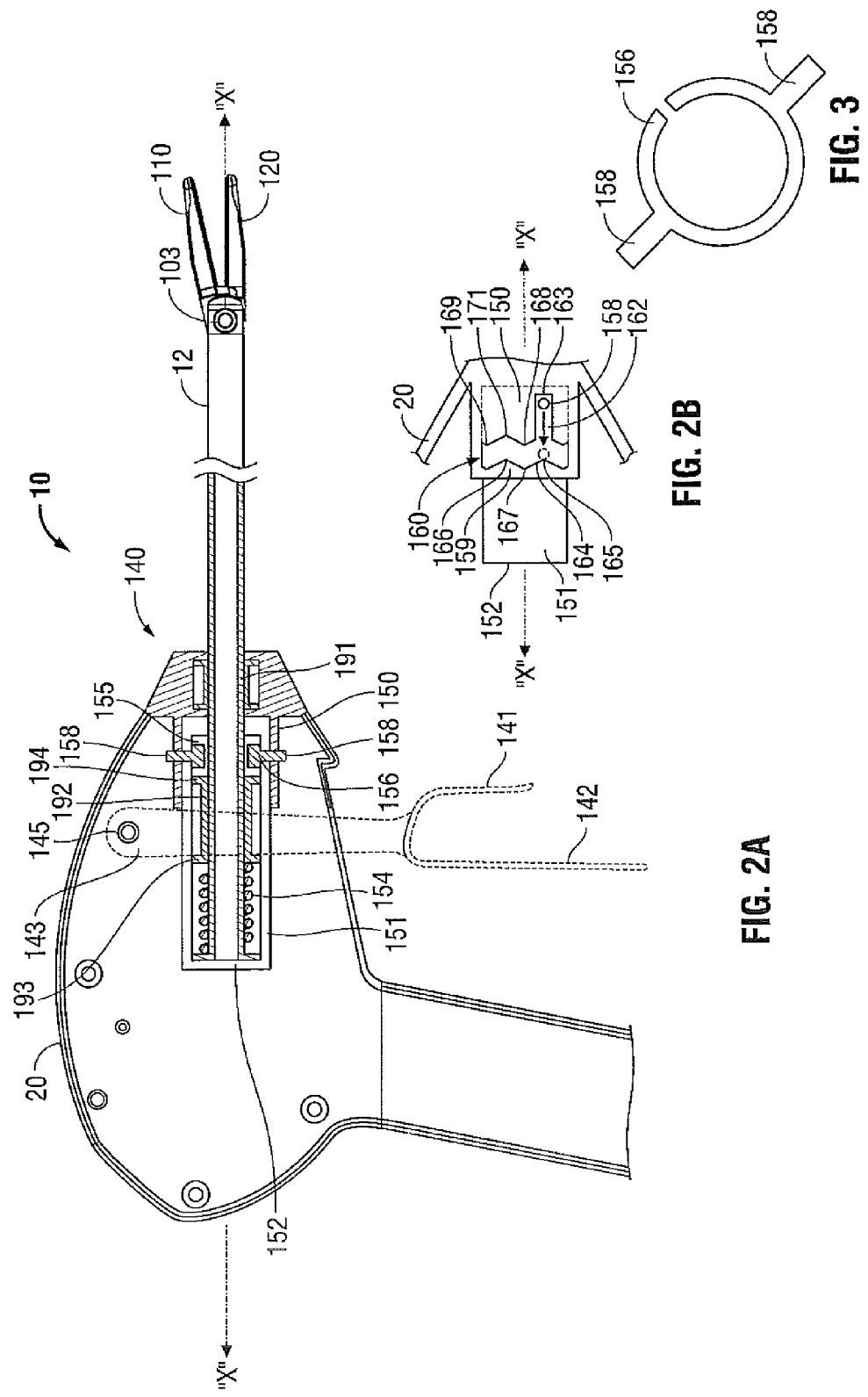

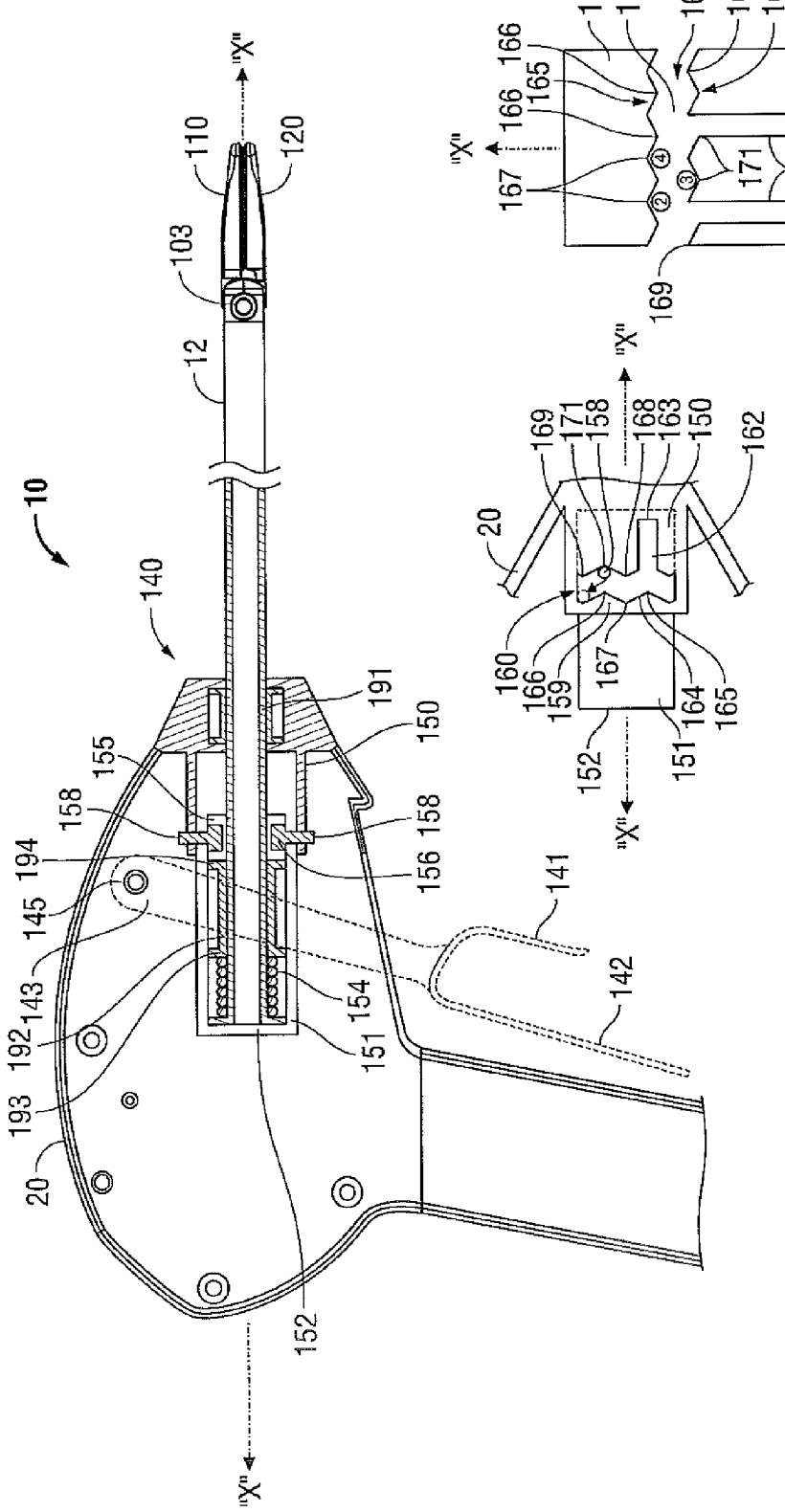

LATCH MECHANISM FOR SURGICAL INSTRUMENTS

BACKGROUND

The present disclosure relates to surgical instruments. More particularly, the present disclosure relates to releasable latch mechanisms for use with surgical instruments.

TECHNICAL FIELD

Electrosurgical instruments, e.g., forceps, utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a surgical instrument including an end effector assembly having a pair of jaw members pivotably coupled to one another. One or both of the jaw members is moveable relative to the other between a spaced-apart position and an approximated position for grasping tissue therebetween. A drive bar defining a longitudinal axis is longitudinally translatable between a distal position and a proximal position for moving the jaw members between the spaced-apart position and the approximated position. A latch mechanism is also provided. The latch mechanism includes a lever that is moveable between an initial position and an actuated position for translating the drive bar between the distal position and the proximal position and, thus, for moving the jaw members between the spaced-apart position and the approximated position. A sleeve is co-axially disposed about the drive bar. The sleeve includes a track extending annularly therearound. More specifically, the track includes one or more substantially radial segments and one or more substantially longitudinal segments. A rotatable collar is interdisposed between the sleeve and the drive bar. The rotatable collar includes one or more stop members extending radially outwardly from an outer periphery thereof. The stop member(s) is engaged within the track and is configured to translate along the track from a first position, corresponding to the initial position of the lever, wherein the stop member(s) is positioned within one of the substantially longitudinal segments, to a second position, corresponding to the actuated position of the lever, wherein the stop member(s) is engaged within one of the substantially radial segments to lock the lever in the actuated position.

In one embodiment, the stop member(s) are configured to translate from the first position to a third position, corresponding to an over-actuated position, and back to the second position such that the stop member(s) is translated along the track from one of the substantially longitudinal segments to one of the substantially radial segments to lock the lever in the actuated position. Similarly, upon movement of the lever from the actuated position to the over-actuated position, e.g., upon movement of the stop member(s) from the second position to the third position, the stop member(s) is translated along the track from the substantially radial segment to one of the substantially longitudinal segments to unlock the lever from the actuated position.

In another embodiment, the track includes a plurality of alternating substantially longitudinal segments and substantially radial segments disposed annularly about the sleeve. The substantially longitudinal segments may be configured to extend distally along the sleeve relative to the substantially radial segments.

In yet another embodiment, a biasing member is annularly disposed between the drive bar and the sleeve. The biasing member is configured to bias the rotatable collar distally relative to the sleeve.

Another embodiment of a surgical instrument in accordance with the present disclosure includes an end effector assembly, a drive bar and a latch mechanism. The end effector assembly includes a pair of jaw members pivotably coupled to one another. One or both of the jaw members are moveable relative to the other between a spaced-apart position and an approximated position for grasping tissue therebetween. The drive bar defines a longitudinal axis and is longitudinally translatable between a distal position and a proximal position for moving the jaw members between the spaced-apart position and the approximated position. The latch mechanism includes a lever that is moveable between an initial position and an actuated position for translating the drive bar between the distal position and the proximal position and, thus, for moving the jaw members between the spaced-apart and approximated positions. The latch mechanism further includes a cartridge including first and second lumens defined therein and extending longitudinally therethrough in substantially parallel orientation relative to one another. The first lumen is configured to slidably receive a portion of the drive bar therethrough. A rotatable post including a fixed end and a free end is slidably disposed within the second lumen of the cartridge and includes a track extending annularly therearound toward the free end thereof. The track includes one or more substantially radial segments and one or more substantially longitudinal segments. One or more stop members are fixedly coupled to the cartridge. More specifically, the stop member(s) extends radially inwardly into the second lumen of the cartridge to engage the track. The stop member(s) is configured to translate along the track from a first position, corresponding to the initial position of the lever, wherein the stop member(s) is positioned within one of the substantially longitudinal segments, to a second position, corresponding to the actuated position of the lever, wherein the stop member(s) is engaged within one of the substantially radial segments to lock the lever in the actuated position.

In one embodiment, the stop member(s) are configured to translate from the first position to a third position, corresponding to an over-actuated position, and back to the second position such that the stop member(s) is translated along the track from one of the substantially longitudinal segments to one of the substantially radial segments to lock the lever in the actuated position. Similarly, upon movement of the lever from the actuated position to the over-actuated position, e.g., upon movement of the stop member(s) from the second position to the third position, the stop member(s) is translated along the track from the substantially radial segment to one of the substantially longitudinal segments to unlock the lever from the actuated position.

In another embodiment, a biasing member is annularly disposed between the drive bar and the cartridge. The biasing member is configured to bias the cartridge distally relative to the rotatable post.

Still another embodiment of a surgical instrument in accordance with the present disclosure includes an end effector assembly, a drive bar, and a latch mechanism. The end effector assembly includes a pair of jaw members pivotably coupled to one another. One (or both) of the jaw members is moveable relative to the other between a spaced-apart position and an approximated position for grasping tissue therebetween. The drive bar, as in the previous embodiments, is longitudinally translatable between a distal position and a proximal position for moving the jaw members between the spaced-apart position and the approximated position and a lever of the latch mechanism, in turn, is moveable between an initial position and an actuated position for translating the drive bar from the distal position to the proximal position. The latch mechanism further includes a post having a fixed end and a free end. The post is pivotable about the fixed end thereof. A sleeve is rotatably and slidably disposed about the post and includes a track defined therein and extending annularly therearound. The track includes one or more substantially radial segments and one or more substantially longitudinal segments. One or more stop members is engaged within the track, the stop member(s) configured to translate along the track from a first position, corresponding to the initial position of the lever, wherein the stop member(s) is positioned within one of the substantially longitudinal segments, to a second position, corresponding to the actuated position of the lever, wherein the stop member(s) is engaged within one of the substantially radial segments to lock the lever in the actuated position.

As in the previous embodiment, the stop member(s) may be configured to translate from the first position to a third position, corresponding to an over-actuated position, and back to the second position such that the stop member(s) is translated along the track from one of the substantially longitudinal segments to one of the substantially radial segments to lock the lever in the actuated position. Similarly, upon movement of the lever from the actuated position to the over-actuated position, e.g., upon movement of the stop member(s) from the second position to the third position, the stop member(s) is translated along the track from the substantially radial segment to one of the substantially longitudinal segments to unlock the lever from the actuated position.

In one embodiment, the lever includes a pair of flanges disposed on either side of the sleeve. Each flange includes a stop members extending inwardly therefrom, e.g., toward the sleeve, such that movement of the lever effects corresponding movement of the stop members along the track.

In another embodiment, a biasing member is disposed between the sleeve and the free end of the post. The biasing member is configured to bias the sleeve distally relative to the post.

In yet another embodiment, an interference member is disposed at the free end of the post. The interference member is configured such that, upon movement of the lever to the actuated position, the interference member is pivoted into engagement with the drive bar to inhibit the drive bar from returning distally, i.e., to retain the drive bar in the proximal position.

In still another embodiment, the latch mechanism further includes an "L"-spring. The "L"-spring includes a first end that is rotatably coupled to the post toward the fixed end of the post, and a second end that has the stop member extending therefrom.

In still yet another embodiment, the lever includes a pair of flanges disposed on either side of the post and coupled between the sleeve and the free end of the post such that movement of the lever effects corresponding movement of the sleeve relative to the stop member, e.g., the "L"-spring, thereby moving the stop member along the track.

Similar to previous embodiments, the track may include a plurality of alternating substantially longitudinal segments and substantially radial segments disposed about the sleeve.

In another embodiment, the track includes a contoured floor to define a three-dimensional track. More specifically, the contoured floor is configured such that the stop member(s) is moved three-dimensionally relative to the track as the stop member(s) is moved along the track between the substantially longitudinal segments and the substantially radial segments thereof.

BRIEF DESCRIPTION OF THE DRAWINGS

Various embodiments of the presently disclosed latch mechanisms are described herein with reference to the drawings, wherein:

FIG. 2A is a side, cross-sectional view of the forceps of FIG. 1A, including a latching mechanism having a lever disposed in an initial position;

FIG. 2B is a schematic illustration of the latch mechanism of FIG. 2A shown in the unlatched condition;

FIG. 3 is an enlarged, top view of a rotatable collar of the latch mechanism of FIG. 2A;

FIG. 6A is a side, cross-sectional view of the latch mechanism of FIG. 2A, wherein the lever has been moved from the actuated position to a position proximal of the actuated position;

FIG. 6B is a schematic illustration of the latch mechanism of FIG. 2A shown transitioning from the latched condition back to the unlatched condition;

FIG. 7 is a schematic illustration showing the latch mechanism of FIG. 2A transitioning from the unlatched condition to the latched condition and back to the unlatched condition;

DETAILED DESCRIPTION

Figure 1A:
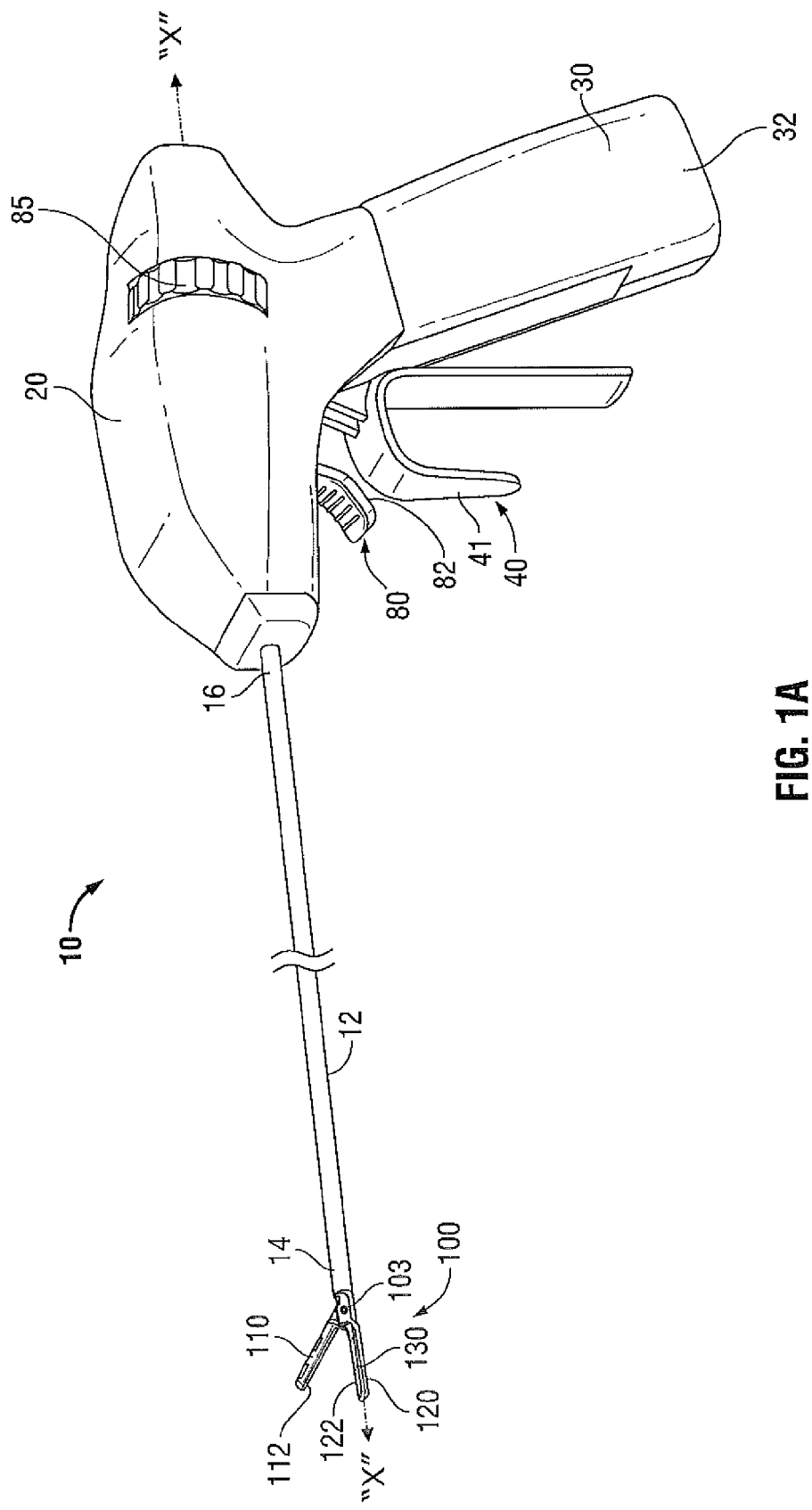
FIG. 1A is a perspective view of a forceps including an end effector assembly in accordance with an embodiment of the present disclosure wherein the jaw members of the end effector assembly are disposed in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1B:
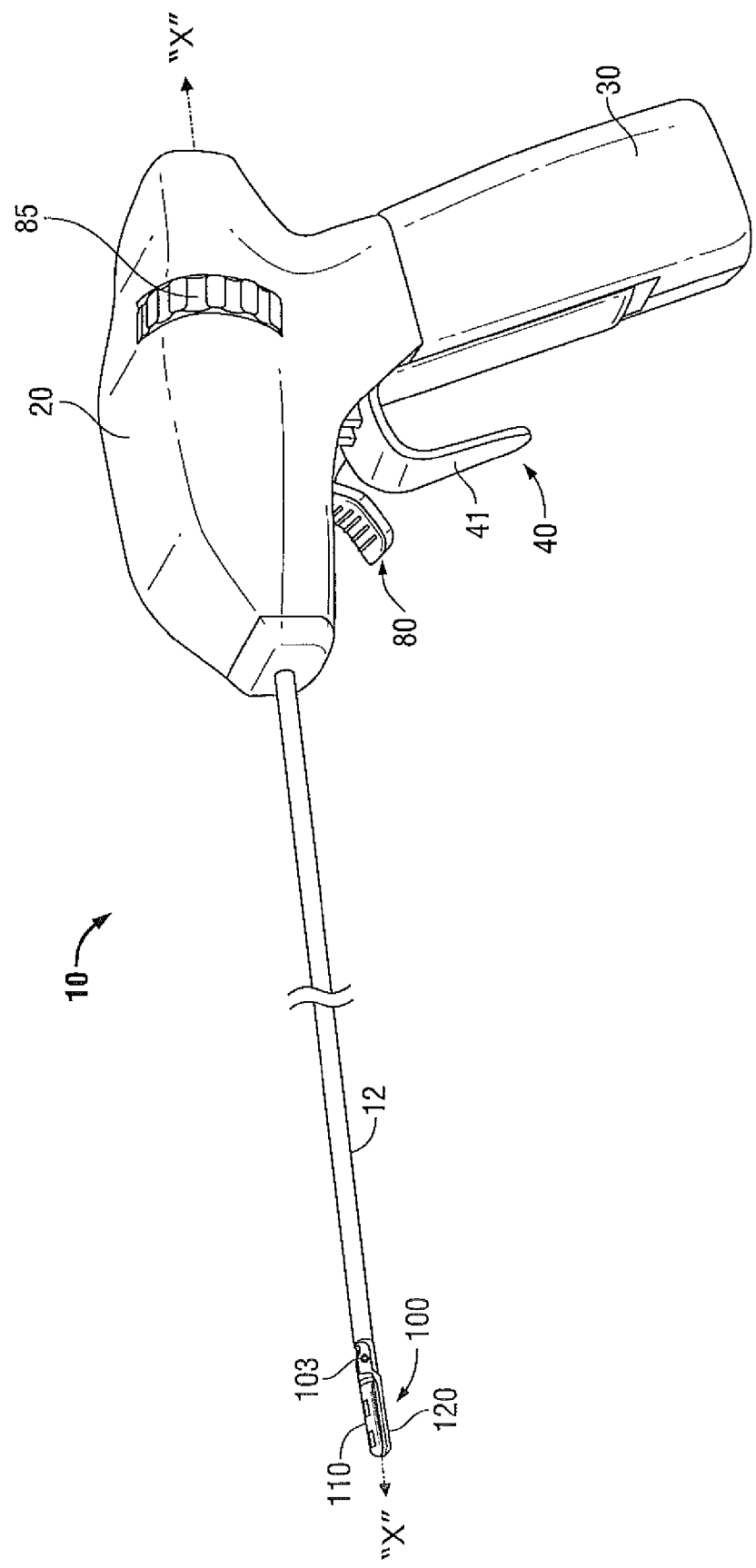
FIG. 1B is a perspective view of the forceps of FIG. 1A wherein the jaw members of the end effector assembly are disposed in an approximated position.

Turning now to FIGS. 1A and 1B, forceps 10 is one example of an instrument for use in accordance with the present disclosure. Forceps 10 including a housing 20, a handle assembly 30, a lever latch assembly 40, a trigger assembly 80, a rotating assembly 85, and an end effector assembly 100. Forceps 10 further includes a shaft 12 having a distal end 14 configured to mechanically engage end effector assembly 100 and a proximal end 16 that mechanically engages housing 20. Alternatively, any surgical instrument having a lever operable to control one or more functions of the end effector assembly may be used in accordance with the present disclosure.

With continued reference to FIGS. 1A and 1B, end effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 relative to jaw member 120. However, either, or both of jaw members 110, 120 may be moveable with respect to the other. In either embodiment, jaw members 110, 120 are moveable from a spaced-apart position, as shown in FIG. 1A, to an approximated position, as shown in FIG. 1B, to grasp tissue therebetween. Further, one or both of jaw members 110, 120 may include an electrically conductive tissue sealing surface 112, 122, respectively. Sealing surfaces 112, 122 are disposed in opposed relation relative to one another such that, with jaw members 110, 120 in the approximated position grasping tissue therebetween, electrosurgical energy may be supplied to one or both of sealing surfaces 112, 122 of jaw members 110, 120, respectively, to seal tissue grasped therebetween.

One or both of jaw members 110, 120 may also include a longitudinally extending blade channel 130 to permit reciprocation of a blade (not shown) therethrough for dividing tissue grasped therebetween. Trigger assembly 80 is operably coupled to the blade (not shown) such that, upon actuation of trigger 82, the blade (not shown) is translated from a retracted position to an extended position wherein the blade (not shown) is advanced between jaw members 110, 120 to cut tissue grasped therebetween. Further, trigger 82 may be biased toward an un-actuated position such that, upon release of trigger 82, the blade (not shown) is returned to the retracted position. A blade-lock feature may also be provided to inhibit translation of the blade to the extended position when jaw members 110, 120 are in the spaced-apart position.

Rotating assembly 85 is integrally associated with housing 20 and is rotatable in either direction about a longitudinal axis "X-X" to rotate jaw members 110, 120 with respect to housing 20 about longitudinal axis "X-X," allowing jaw members 110, 120 to be repositioned relative to tissue to be grasped, sealed and/or divided.

Handle assembly 30 extends downwardly from housing 20 and is releasably engageable with housing 20. Handle assembly 30 is ergonomically configured such that, when engaged with housing 20, a surgeon may grasp handle assembly 30 and operate lever latch assembly 40, trigger assembly 80 and/or rotating assembly 85 with a single hand. Handle assembly 30 may further includes a battery pack (not shown) disposed within a battery housing 32. The battery pack (not shown) of handle assembly 30 provides power to forceps 10, e.g., for energizing sealing surfaces 112, 122 of jaw members 110, 120, respectively. More particularly, the battery pack (not shown) may be configured to electrically couple to a generator (not shown) disposed within housing 20 for powering the generator (not shown). The generator (not shown), in turn, supplies the desired energy to sealing surfaces 112, 122 of jaw members 110, 120, respectively, of end effector assembly 100. Alternatively, forceps 10 may be configured to connect to an external energy source (not shown), e.g., via an electrosurgical cable (not shown), obviating the need for the battery pack (not shown) and generator (not shown) to be disposed within handle assembly 30 and housing 20, respectively.

With continued reference to FIGS. 1A and 1B, battery housing 32 of handle assembly 30 may include mechanical keying features (not shown) configured complementarily to mechanical keying features associated with housing 20 such that handle assembly 30 may be securely locked in mechanical engagement with housing 20. Upon such engagement, the battery pack (not shown) is electrically coupled to the generator (not shown). The battery housing 32 may also be released from housing 20, e.g., to replace or recharge the battery pack (not shown).

Continuing with reference to FIGS. 1A and 1B, lever latch assembly 40 includes a lever 41 pivotably coupled to housing 20 and extending downwardly therefrom. Lever 41 is ultimately connected to a drive assembly that, as will be described in greater detail below, together mechanically cooperate to impart movement of jaw members 110 and 120 between the spaced-apart position (FIG. 1A) and the approximated position (FIG. 1B). More particularly, lever 41 is selectively moveable from an initial position (FIG. 1A), wherein lever 41 is spaced-apart from handle assembly 30, to an actuated position (FIG. 1B), wherein lever 41 is positioned adjacent handle assembly 30, to move jaw members 110, 120 from the spaced-apart position (FIG. 1A) to the approximated position (FIG. 1B). Lever latch assembly 40 is configured to permit movement of lever 41 between the initial position and the actuated position and for releasably locking lever 41 in the actuated position. In other words, lever latch assembly 40 is configured to selectively move jaw members 110, 120 between the spaced-apart position and the approximated position and to releasably lock jaw members 110, 120 in the approximated position. Further, lever 41 may be biased toward the initial position, such that jaw members 110, 120 are biased toward the spaced-apart position. Various embodiments of lever latching assemblies configured for use with forceps 10 (or other suitable surgical instruments (not shown)) will be described below with reference to FIGS. 2A-20B.

With reference now to FIGS. 2A-7, and initially to FIG. 2A, one embodiment of a lever latch assembly in accordance with the present disclosure, lever latch assembly 140, is shown. Lever latch assembly 140 includes a lever 141 that is pivotably coupled to housing 20 and extends downwardly therefrom. More specifically, lever 141 includes a grasping portion 142 that extends downwardly from housing 20, and first and second flanges 143 that extend upwardly from grasping portion 142 into housing 20. Flanges 143 extend upwardly on either side of drive bar 191, ultimately engaging pivot pin 145 on either end thereof, thus allowing lever 141 to pivot about pivot pin 145 relative to housing 20.

Continuing with reference to FIG. 2A, drive bar 191 is disposed about longitudinal axis "X-X" and extend distally through housing 20 and shaft 12, ultimately coupling to jaw member 110 (and/or jaw member 120) of end effector assembly 100. More specifically, drive bar 191 is pivotably engaged to jaw member 110 at a position offset relative to pivot pin 103 such that proximal translation of drive bar 191 pulls jaw member 110 to rotate in a first direction about pivot pin 103 relative to jaw member 120, e.g., from the spaced-apart position (FIG. 1A) to the approximated position (FIG. 1B) and such that distal translation of drive bar 191 pushes jaw member 110 to rotate about pivot pin 103 in the opposite direction, e.g., from the approximated position to the spaced-apart position. The reverse configuration, e.g., wherein distal translation of drive bar 191 effects closure of jaw members 110, 120 and where proximal translation of drive bar 191 opens jaw members 110, 120 and other suitable drive mechanisms (not shown) are also contemplated.

As shown in FIG. 2A, a mandrel 192 is disposed about drive bar 191 toward a proximal end thereof and includes proximal and distal rims 193, 194, respectively, Mandrel 192 is fixedly engaged to drive bar 191 and is annularly disposed between drive bar 191 and flanges 143 of lever 141. Proximal and distal rims 193, 194, respectively, of mandrel 192 extend radially outwardly therefrom to retain flanges 143 of lever 141 therebetween. Accordingly, as lever 141 is moved proximally, e.g., as lever 141 is pivoted about pivot pin 145 from the initial position to the actuated position, flanges 143 contact proximal rim 193 of mandrel 192 and urge drive bar 191 proximally. On the other hand, as lever 141 is moved distally, e.g., as lever 141 is returned to the initial position, flanges 143 contact distal rim 194 of mandrel 192 and urge drive bar 191 distally. Put more generally, mandrel 192 couples flanges 143 of lever 141 to drive bar 191 such that jaw members 110, 120 are moved from the spaced-apart position (FIG. 1A) to the approximated position (FIG. 1B) as lever 141 is moved from the initial position to the actuated position and such that jaw members 110, 120 are moved from the approximated position (FIG. 1B) back to the spaced-apart position (FIG. 1A) as lever 141 is returned from the actuated position back to the initial position.

With reference now to FIGS. 2A-3, housing 20 of forceps 10 includes an outer sleeve 150 disposed therein and fixedly engaged thereto and an inner sleeve 151 disposed within outer sleeve 150 and engaged to drive bar 191. Outer and inner sleeves 150, 151, respectively, are centered about longitudinal axis "X-X." Inner sleeve 151, drive bar 191, and mandrel 192 are slidably disposed within outer sleeve 150 such that proximal and distal rims 193, 194, respectively, of mandrel 192 protrude radially outwardly from the open lateral sides of inner sleeve 151, allowing flanges 143 of lever 141 to engage mandrel 192 and, thus, drive bar 191, externally of outer sleeve 150. Further, a biasing member, e.g., spring 154, is disposed between proximal wall 152 of inner sleeve 151 and proximal flange 193 of mandrel 192 to bias drive bar 191 toward a distal position, e.g., to bias jaw members 110, 120 toward a spaced-apart position. As can be appreciated, as lever 141 is moved from the initial position to the actuated position, mandrel 192 and drive bar 191 are translated proximally relative to outer and inner sleeves 150, 151, respectively, against the bias of spring 154 to move jaw members 110, 120 from the spaced-apart position to the approximated position. Likewise, when lever 141 is released, mandrel 192 and drive bar 191 are translated distally relative to outer and inner sleeves 150, 151, respectively, under the bias of spring 154, to return jaw members 110, 120 to the spaced-apart position.

Continuing with reference to FIGS. 2A-3, mandrel 192 further includes a distal extension 155 extending distally therefrom. Distal extension 155 of mandrel 192 is configured to retain a rotatable collar 156 therein. Rotatable collar 156 is longitudinally fixed relative to mandrel 192 and drive bar 191 but is permitted to rotate about longitudinal axis "X-X" relative to mandrel 192 and drive bar 191. As best shown in FIG. 3, rotatable collar 156 includes a pair of diametrically-opposed stop members 158 extending radially outwardly from an outer periphery thereof. Although two stop members 158 are shown, greater or fewer than two stop members 158 may also be provided.

Stop members 158, as mentioned above, extend radially outwardly from rotatable collar 156 to engage track 160 defined within outer sleeve 150. More specifically, proximal portion 159 of outer sleeve 150 includes a track 160 extending annularly therearound and configured to retain stop members 158 therein. As will be described in greater detail below, once lever 141 is moved from the initial position past the actuated position, e.g., to the over-actuated position, stop members 158 of rotatable collar 156 are translated along and rotated relative to track 160 of proximal portion 159 of outer sleeve 150. Thereafter, lever 141 may be released such that stop members 158 are engaged within track 160 to latch lever 141 in the actuated position, releasably latching jaw members 110, 120 in the approximated position. Upon further actuation of lever 141, followed by release of lever 141, stop members 158 of rotatable collar 156 are further translated along and rotated relative to track 160 of distal portion 159 of outer sleeve 150 to unlatch lever latch assembly 140, allowing lever 141 to return to the initial position and allowing jaw members 110, 120 to return to the spaced-apart position.

Referring once again to FIGS. 2A-7, the use and operation of lever latch assembly 140 will be described. Initially, as shown in FIG. 2A, lever 141 is disposed in the initial position, jaw members 110, 120 are disposed in the spaced-apart position, and stop members 158 of rotatable collar 156 are disposed at distal ends 163 of longitudinal segments 162 of track 160 of outer sleeve 150 (FIGS. 2B and 7). In this position, forceps 10 may be manipulated and/or end effector assembly 100 may be rotated to position jaw members 110, 120 such that tissue to be grasped, sealed and/or divided is disposed therebetween.

Figures 4A, 4B:
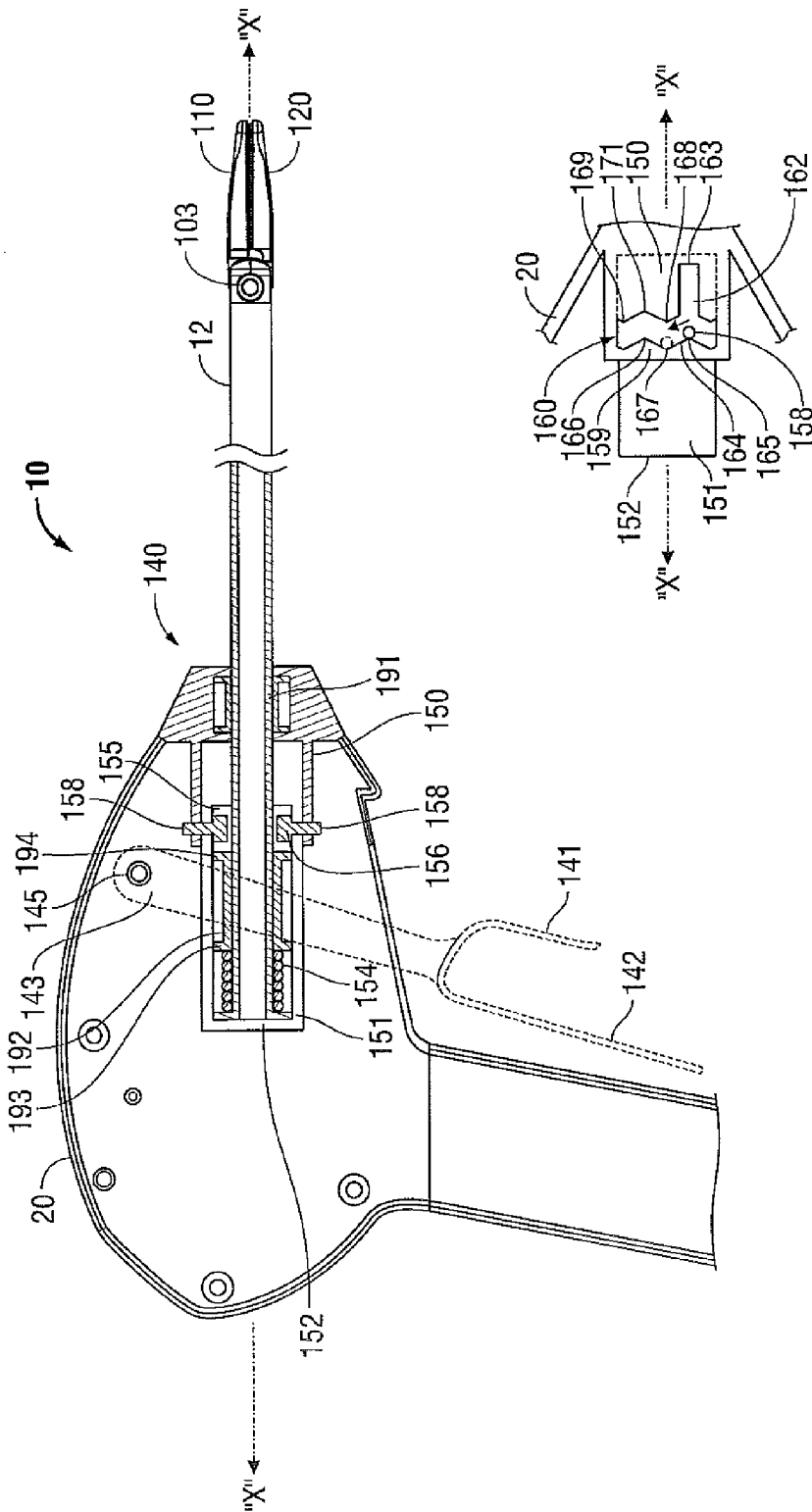
FIG. 4A is a side, cross-sectional view of the latch mechanism of FIG. 2A, wherein the lever is disposed in an actuated position.
FIG. 4B is a schematic illustration of the latch mechanism of FIG. 2A shown transitioning between the unlatched condition and the latched condition.

Once end effector assembly 100 is positioned as desired, e.g., with tissue disposed between jaw members 110, 120, jaw members 110, 120 may be moved to the approximated position to grasp tissue. To move jaw members 110, 120 to the approximated position, lever 141 is pulled proximally from the initial position toward the actuated position, as shown in FIG. 4A. As lever 141 is pulled toward the actuated position, mandrel 192, drive bar 191, and collar 156 are translated proximally against the bias of spring 154, pulling jaw member 110 to rotate about pivot pin 103 relative to jaw member 120 toward the approximated position. At the same time, stop members 158 of rotatable collar 156 are translated proximally along longitudinal segment 162 of track 160 of outer sleeve 150.

Lever 141 is moved further proximally past the actuated position such that mandrel 192, drive bar 191, and rotatable collar 156 are likewise translated further proximally to move jaw members 110, 120 into further approximation with one another. More specifically, lever 141 is moved proximally past the actuated position until stop members 158 have been translated proximally completely through longitudinal segments 162 of track 160 and into abutment with proximal surface 165 of annular segment 164 of track 160, as best shown in FIG. 4B and FIG. 7 (position 2). This position corresponds to the over-actuated position, e.g., where lever 141 has been moved proximally beyond the actuated position and is inhibited from being depressed further due to the engagement of stop members 158 within proximal surface 165 of track 160. Proximal surface 165 of annular segment 164 of track 160 defines a triangle-wave-shaped configuration including a plurality of alternative peaks 166 and valleys 167. Accordingly, when stop members 158 contact proximal surface 165 of track 160, due to the triangle-wave-shaped configuration of proximal surface 165 of track 160, stop members 158 are urged along the angled proximal surface 165 from the peaks 166 of proximal surface 165 to the valleys 167 thereof. In other words, upon movement of lever 141 to the over-actuated position, stop members 158 are urged into contact with proximal surface 165 track 160 and are translated annularly along track 160 such that rotatable collar 156 is rotated about longitudinal axis "X-X" relative to outer sleeve 150. As can be appreciated, with rotatable collar 156 having been rotated about longitudinal axis "X-X" relative to outer sleeve 150, stop members 158 are no longer longitudinally aligned with longitudinal segments 162 of track 160.

Figures 5A, 5B:
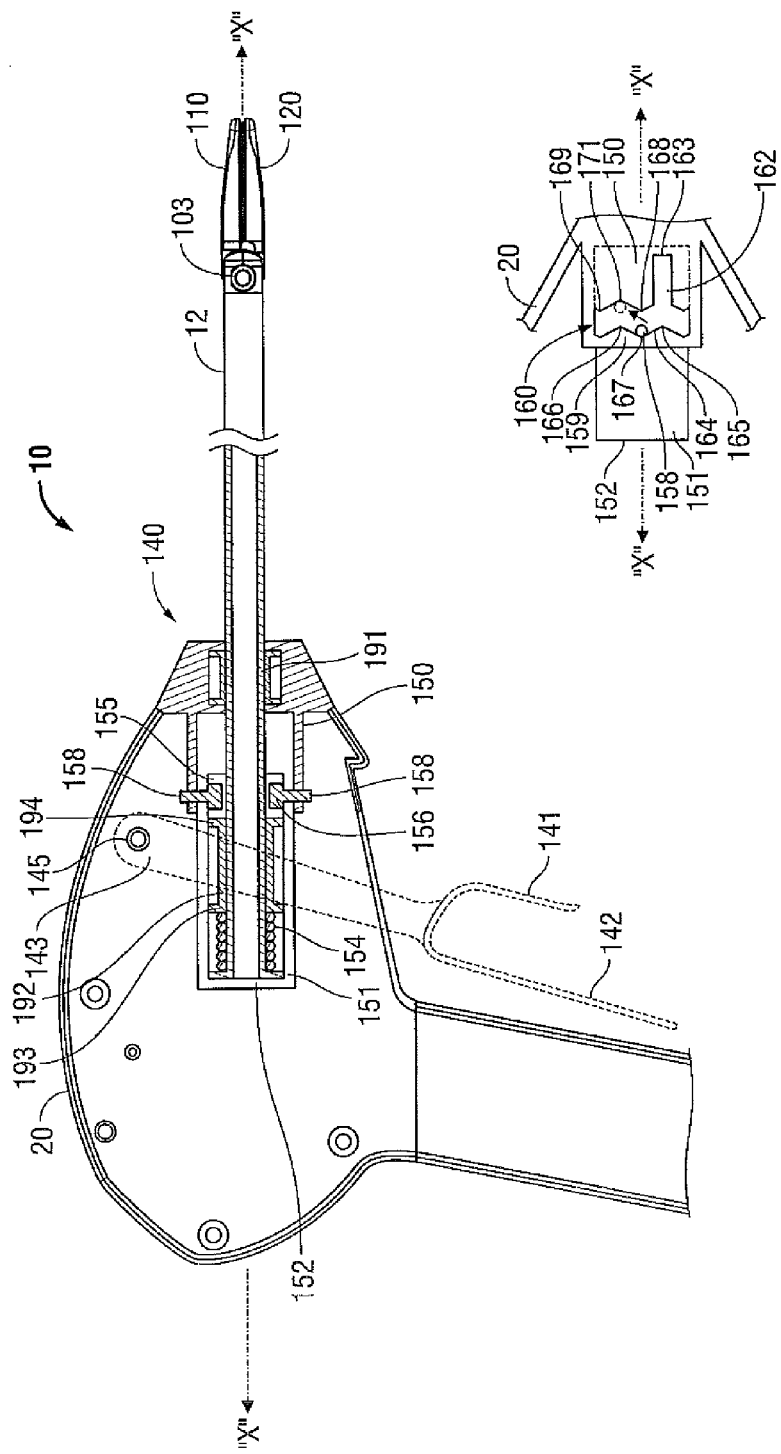
FIG. 5A is a side, cross-sectional view of the latch mechanism of FIG. 2A wherein the lever has been moved to the actuated position and has thereafter been released.
FIG. 5B is a schematic illustration of the latch mechanism of FIG. 2A shown disposed in the latched condition.

As shown in FIG. 5B, upon release of lever 141 from the over-actuated position, e.g., allowing spring 154 to urge lever 141 distally back to the actuated position, stop members 158 are translated distally relative to track 160. However, with stop members 158 no longer aligned with longitudinal segments 162 of track 160, lever 141 is only permitted to return distally to the actuated position, wherein stop members 158 contact distal surface 168 of track 160 inhibiting further distal movement. More specifically, similar to proximal surface 165 of track 160, distal surface 168 of track 160 defines a triangle-wave-shaped configuration. As a result, as stop members 158 are urged into contact with distal surface 168 of track 160, rotatable collar 156 is rotated about longitudinal axis "X-X" such that stop members 158 are translated from the peaks 169 of distal surface 168 of track 160 to the valleys 171 thereof. Once rotated into position, stop members 158 are retained in the valleys 171 of distal surface 168 of track 160 under the bias of spring 154. The engagement of stop members 158 within valleys 171 of distal surface of track 160 (FIG. 7) inhibits stop members 158, lever 141, and drive bar 191 from returning distally. This position corresponds to the actuated position of lever 141 and the approximated position of jaw members 110, 120. In other words, the engagement of stop members 158 within distal surface 168 of track 160 latches jaw members 110, 120 in the approximated position.

With jaw members 110, 120 latched in the approximated position grasping tissue therebetween, electrosurgical energy may be supplied to one or both of sealing surfaces 112, 122 of jaw members 110, 120, respectively, of end effector assembly 100 to effect a tissue seal (see FIGS. 1A-1B). Thereafter, as mentioned above, a knife (not shown) may be advanced between jaw members 110, 120 to divide the previously sealed tissue.

With lever latch assembly 140 in the latched condition, as described above, the surgeon need not retain lever 141 in the actuated position during sealing and/or dividing of tissue. Such a feature helps reduces surgeon fatigue and helps ensure that a consistent and accurate closure force between jaw members 110, 120 is applied. As can be appreciated, the length of longitudinal segments 162 of track 160 may be selected to achieve a specific closure force between jaw members 110, 120 when moved to the approximated position. As such, outer sleeve 150 may be configured as an interchangeable component that is releasably engageable to housing 20, allowing the user to select the desired outer sleeve 150 in accordance with the desired closure force between jaw members 110, 120 when in the approximated position.

The above-described lever latch assembly 140 may be selectively used by the surgeon. For example, where it is desirable to retain jaw members 110, 120 in the approximated position upon each stroke of lever 141, the surgeon may simply translate lever 141 from the initial position to the over-actuated position, e.g., the proximal-most position, and may thereafter release lever 141 such that lever 141 is latched in the actuated position and such that jaw members 110, 120 are latched in the approximated position. On the other hand, where repeated and/or rapid tissue sealing is desired, the surgeon may depress lever 141 to the actuated position (but not the over-actuated position) to move jaw members 110, 120 to the approximated position. In this configuration, upon release of lever 141, since lever 141 and jaw members 110, 120 are not latched, lever 141 and jaw members 110, 120 are returned to the initial position and the spaced-apart position, respectively. This operation may then be repeated to grasp, seal and/or divide numerous portions of tissue, without requiring lever latch assembly 140 to be unlatched after each successive operation. Further, audible and/or tactile feedback may be provided to alert the surgeon as to the position of stop members 158 relative to track 160, e.g., to notify the surgeon as to when lever 141 has reached the actuated position and/or the over-actuated position.

Turning now to FIGS. 6A-6B, in order to unlatch lever latch assembly 140, lever 141 is pulled proximally from the actuated position to the over-actuated position such that mandrel 192, drive bar 191 and rotatable collar 156 are moved proximally. Likewise, stop members 158 are translated proximally from valleys 171 of distal surface 168 of track 160 until stop members 158 contact proximal surface 165 of track 160. Once again, the triangle-wave-shaped configuration of proximal surface 165 of track 160 urges rotatable collar 156 to rotate about longitudinal axis "X-X" as stop members 158 are translated from the peaks 166 of proximal surface 165 of track 160 to the valleys 167 thereof. Once lever 141 has been moved proximally back to the over-actuated position, lever 141 may be released, allowing mandrel 192, drive bar 191, and rotatable collar 156 to return distally under the bias of spring 154. As mandrel 192 and drive bar 191 are returned distally, jaw members 110, 120 are moved back toward the spaced-apart position. Eventually, upon further distal translation, stop members 158 contact triangle-wave-shaped distal surface 168 of track 160. The triangle-wave-shaped configuration of distal surface 168 of track 160 urges stop members 158 and, thus, collar 156 to once again rotate relative to track 160. More specifically, triangle-wave-shaped distal surface 168 urges stop members 158 to rotate back into alignment with longitudinal segments 162 of track 160. Accordingly, with stop members 158 aligned with longitudinal segments 162 of track 160, lever 141, mandrel 192, drive bar 191 and rotatable collar 156 are permitted to translate further distally under the bias of spring 154 as stop members 158 are translated distally through longitudinal segments 162 of track 160 until lever 141 returns to the initial position. At the same time, jaw members 110, 120 are moved apart from one another, eventually returning to the spaced-apart position.

With reference now to FIG. 7, a schematic illustration of track 160 is shown. Although track 160 extends annularly about outer sleeve 150, it is shown in a linear orientation for illustration purposes. As shown in FIG. 7, the triangle-wave-shaped configurations of proximal and distal surfaces 165, 168, respectively, of track 160 are offset relative to one another such that, as stop members 158 are longitudinally translated into contact with proximal and distal surfaces 165, 168, respectively, of track 160, rotatable collar 156 is urged to rotate about longitudinal axis "X-X," e.g., such that stop members 158 are moved from longitudinal segments 162 of track 160 to the annular segments 164 of track 160. Further, the number of longitudinal and annular segments 162, 164, respectively, may be varied. More specifically, track 160 may include a pair of alternating longitudinal segments 162 and annular segments 164 such that rotatable collar 156 is rotated through one complete revolution about longitudinal axis "X-X" upon movement of lever 141 through one cycle, e.g., from the initial position to the over-actuated position back the actuated position and from the actuated position to the over-actuation position back to the initial position. However, track 160 may alternatively be configured to include four alternating longitudinal segments 162 and annular segments 164 such that rotatable collar 156 is rotated one-half a revolution per cycle of lever 141, or track 160 may define various other configurations.

Referring now to FIGS. 8-11, another embodiment of a lever latch assembly configured for use with forceps 10 is shown generally identified by reference numeral 240. Lever latch assembly 240, similar to lever latch assembly 140 (FIGS. 2A-7) includes a lever 241 that is pivotably coupled to housing 20 of forceps 10 via pivot pin 245 and is configured to move between an initial position and an actuated position for translating drive bar 291 between a distal position and a proximal position to move jaw members 110, 120 (FIGS. 1A-1B) between the spaced-apart position (FIG. 1A) and the approximated position (FIG. 1B).

Similar to the previous embodiment, lever 241 includes a pair of flanges 243 extending upwardly on either side of drive bar 291. Lever latch assembly 240 further includes a cartridge 250 having first and second sleeves 252, 260, respectively, extending longitudinally therethrough in generally parallel orientation relative to one another. First sleeve 252 is centered about longitudinal axis "X-X" (see FIGS. 1A and 1B) and is configured for fixedly receiving drive bar 291 therethrough. More specifically, cartridge 250 is interdisposed between drive bar 291 and flanges 243 of lever 241 and includes proximal and distal shoulders 253, 255, respectively, configured to retain flanges 243 of lever 241 therebetween. Accordingly, when lever 241 is moved from the initial position to the actuated position, flanges 243 contact proximal shoulder 253 of cartridge 250 and urge drive bar 291 proximally to move jaw members 110, 120 toward the approximated position (FIG. 1B). On the other hand, when lever 241 is returned from the actuated position back to the initial position, flanges 243 contact distal shoulder 255 of cartridge 250 and urge drive bar 291 distally to move jaw members 110, 120 back toward the spaced-apart position (FIG. 1A). Further, a spring 254 (or other biasing member) may be disposed within cartridge 250 to bias cartridge 250 and drive bar 291 distally. As such, with flanges 243 of lever 241 engaged between shoulders 253, 255 of cartridge 250, spring 254 also biases lever 241 toward the initial position and jaw members 110, 120 toward the spaced-apart position (FIG. 1A).

With continued reference to FIGS. 8-11, second sleeve 260 of cartridge 250 is configured to slidably receive free end 263 of post 262 therethrough. Post 262 is rotatably coupled to housing 20 of forceps 10 at a fixed end 264 thereof and extends proximally therefrom to free end 263. Further, post 262 includes a track 270 defined therein, extending annularly therearound, and disposed toward free end 263 thereof. A pair of opposed stop members 278 disposed on cartridge 250 and extending radially inwardly into second sleeve 260 are engaged within track 270 of post 262. More specifically, as described above with respect to lever latch assembly 140, stop members 278 of cartridge 250 are configured to translate along track 270 upon translation of cartridge 250 relative to post 262, e.g., upon movement of lever 241 from the initial position to the actuated position. Track 270 is configured substantially similarly to track 160 (FIG. 7) and stop members 278 are configured to translate and rotate relative to track 270 to latch and unlatch lever latch assembly 240 in a similar fashion as described above with respect to lever latch assembly 140 (see FIGS. 2A-7). In particular, as will be described in greater detail below, as stop members 278 of cartridge 250 are translated along track 270, post 262 is urged to rotate relative to cartridge 250 and, thus, stop members 278 such that lever 241 may be latched in the actuated position, thereby latching jaw members 110, 120 in the approximated position (FIG. 1B). Thus, different from lever latch assembly 140 (FIGS. 2A-7), stop members 278 are fixed relative to housing 20 of forceps 10, while track 270 is translatable and rotatable relative to stop members 278 upon latching and unlatching of lever latch assembly 240. Lever latch assembly 240 may otherwise include any of the features of lever latch assembly 140, discussed above, and vice versa.

Figure 8:
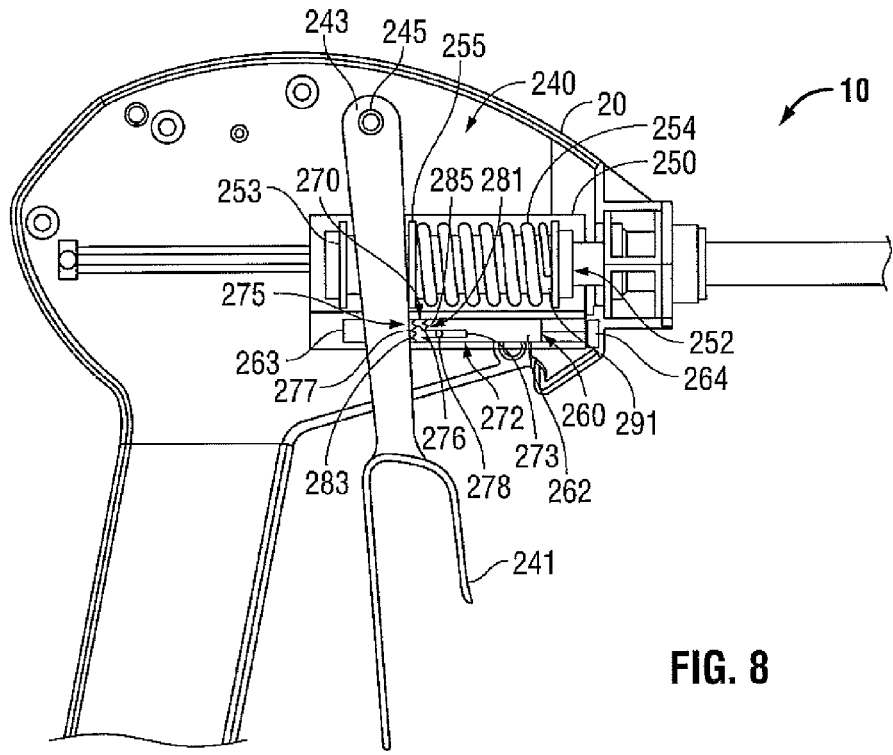
FIG. 8 is a side, cut-away view of an other embodiment of a latch mechanism configured for use with the forceps of FIG. 1A, wherein the lever is disposed in an initial position.

Continuing with reference to FIGS. 8-11, the use and operation of lever latch assembly 240 will be described. Initially, as shown in FIG. 8, lever 241 is disposed in the initial position, cartridge 250 and drive bar 291 are disposed in the distal position and jaw members 110, 120 are disposed in the spaced-apart position (FIG. 1A). Further, in this position, stop members 278 are disposed at the distal ends 273 of longitudinal segments 272 of track 270 of post 262.

Figure 9:
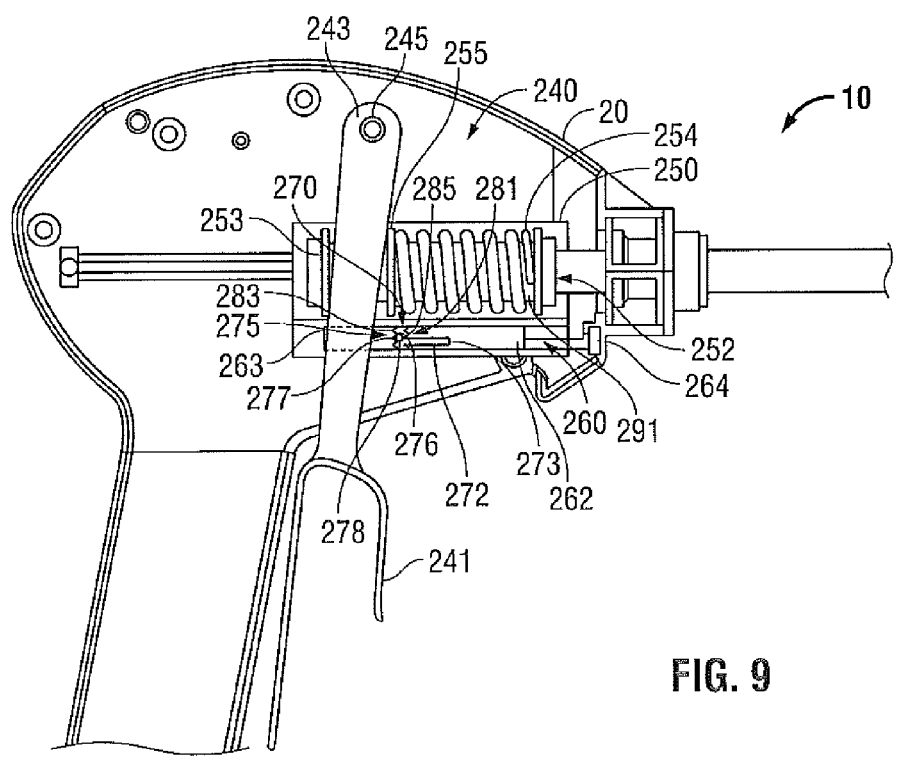
FIG. 9 is a side, cut-away view of the latch mechanism of FIG. 8, wherein the lever has been moved to the actuated position.
Figure 10:
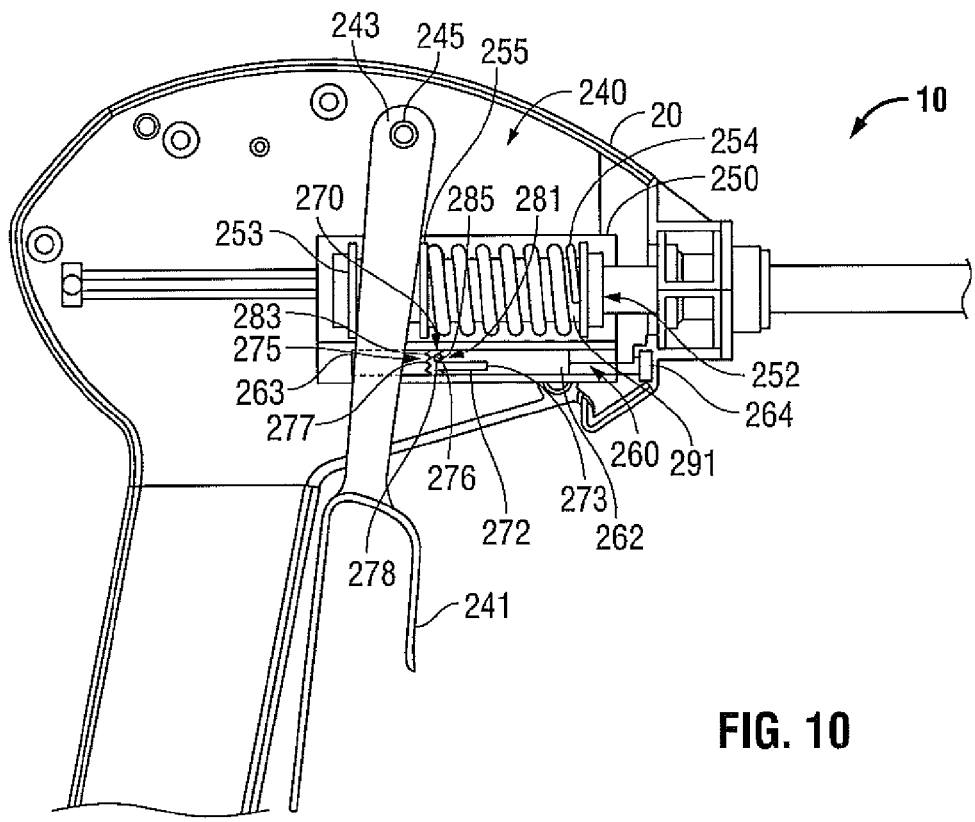
FIG. 10 is a side, cut-away view of the latch mechanism of FIG. 8, wherein the latch mechanism is disposed in the latched condition, retaining the lever in the actuated position.

Turning now to FIG. 9, when it is desired to move jaw members 110, 120 to the approximated position, e.g., to grasp tissue between sealing surfaces 112, 122 of jaw members 110, 120, respectively, (see FIGS. 1A-1B) lever 241 is moved proximally from the initial position toward the actuated position. As mentioned above, moving lever 241 from the initial position toward the actuated position translates cartridge 250 and, thus, drive bar 291 proximally to pivot jaw member 110 about pivot pin 103 toward jaw member 120 (see FIG. 1B). At the same time, cartridge 250 is translated proximally relative to post 262 such that stop members 278 are translated proximally along longitudinal segments 272 of track 270. Lever 241 is moved further proximally past the actuated position until stop members 278 have translated proximally completely through longitudinal segments 272 of track 270 and into abutment with proximal surface 275 of track 270 (the over-actuated position). As stop members 278 contact the triangle-wave-shaped proximal surface 275 of track 270, post 262 is urged to rotate relative to stop members 278 such that stop members 278 are translated along track 270 of post 262 from the peaks 276 of proximal surface 275 of track 270 to the valleys 277 thereof. In this position, due to the rotation of post 262 relative to stop members 278, stop members 278 are no longer aligned with longitudinal segments 272 of track 270.

Once this over-actuated position has been achieved, lever 241 may be released, allowing lever 241 to return distally toward the actuated position under the bias of spring 254. As lever 241 is translated distally, stop members 278 are likewise translated distally relative to track 270 of post 262, eventually contacting distal surface 281 of track 270, which inhibits further distal translation of lever 241. Once again, due to the triangle-wave-shaped configuration of distal surface 281 of track 270, stop members 278 are urged from the peaks 283 of distal surface 281 of track 270 to the valleys 285 thereof, urging post 262 to rotate relative to stop members 278. Stop members 278 are retained in the valleys 285 of distal surface 281 of track 270 under the bias of spring 254 such that lever 241 is latched in the actuated position and such that cartridge 250 and drive bar 291 are inhibited from returning distally. Accordingly, with stop members 278 retained within valleys 285 of distal surface 281 of track 270, jaw members 110, 120 are latched in the approximated position (see FIG. 18). As discussed above, with jaw members 110, 120 latched in the approximated position grasping tissue therebetween, forceps 10 may be used to seal and/or divide tissue grasped between jaw members 110, 120 (see FIG. 1B).

Figure 11:
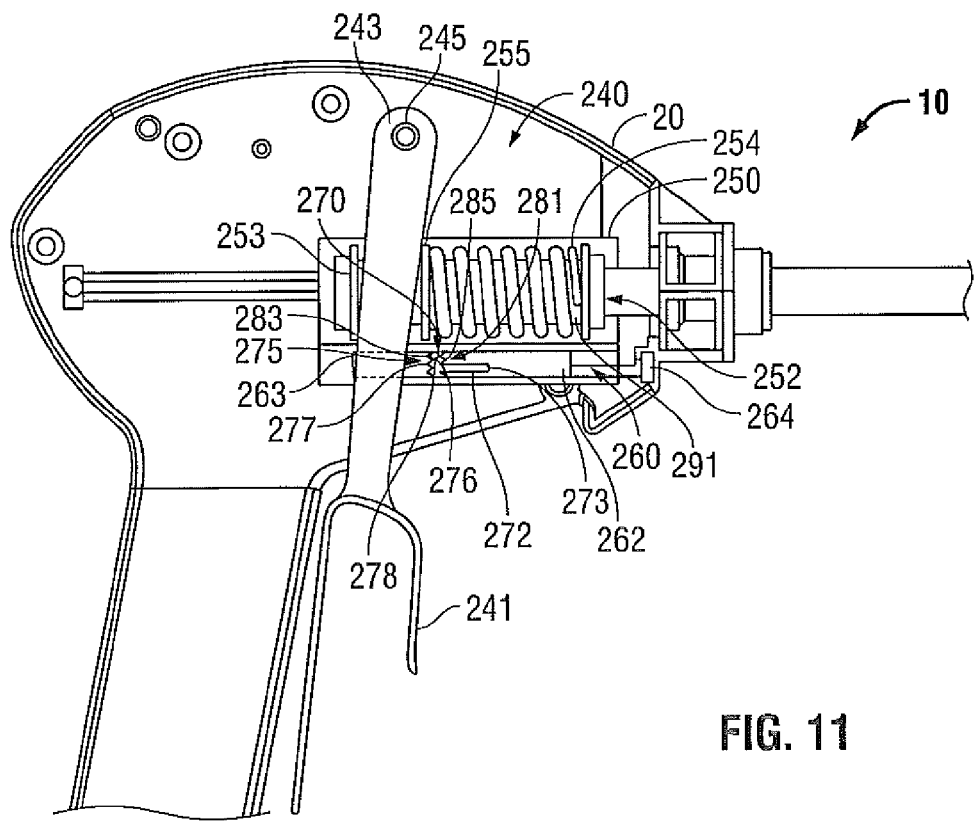
FIG. 11 is a side, cut-away view of the forceps of FIG. 8, wherein the lever has been moved from the actuated position to a position proximal of the actuated position to unlatch the latch mechanism.

Turning now to FIG. 11, in order to unlatch lever latch assembly 240, lever 241 is pulled proximally from the actuated position to the over-actuated position such that stop members 278 are translated proximally from valleys 285 of distal surface 281 of track 270 into contact with proximal surface 275 of track 270. Upon contacting proximal surface 275 of track 270, the triangle-wave-shaped proximal surface 275 of track 270 urges post 262 to rotate relative to stop members 278 such that stop members 278 are moved along track 270 from the peaks 276 of proximal surface 275 of track 270 to the valleys 277 thereof. This rotation of post 262 relative to stop members 278 aligns stop members 278 with distally-sloping portions of the triangle-wave-shaped distal surface 281 of track 270. The distally-sloping portions of distal surface 281 of track 270 feed into longitudinal segments 272 of track 270. As such, upon release of lever 241 from the over-actuated position, stop members 278 are translated proximally into contact with distal surface 281 of track 270, rotating post 262 relative to stop members 278. Eventually, post 262 is rotated sufficiently such that stop members 278 are once again aligned with longitudinal segments 272 of track 270. Once this alignment is achieved, cartridge 250 and drive bar 291 are permitted to translate distally under the bias of spring 254 as stop members 278 are translated distally through longitudinal segments 272 of track 270. At the same time, lever 241 is returned to the initial position and jaw members 110, 120 are returned to the spaced-apart position.

Turning now to FIGS. 12-15, yet another embodiment of a lever latch assembly configured for use with forceps 10 is shown. Similar to lever latch assembly 140, lever latch assembly 340 includes a lever 341 that is pivotably coupled to housing 20 and extends downwardly therefrom. Lever 341 includes a pair of flanges 343 that extend upwardly on either side of drive bar 391, ultimately engaging pivot pin 345 on either end thereof. Lever 341 is pivotable about pivot pin 345 relative to housing 20 between an initial position and an actuated position. Similarly as discussed above, flanges 343 of lever 341 are coupled to drive bar 391 via a mandrel 392 such that moving lever 341 from the initial position to the actuated position translates drive bar 391 proximally to move jaw members 110, 120 toward the approximated position. On the other hand, moving lever 341 from the actuated position back to the initial position translates drive bar 391 distally to move jaw members 110, 120 back toward the spaced-apart position.

Housing 20 further includes a cartridge 350 disposed therein and configured for longitudinal translation along longitudinal axis "X-X." Cartridge 350 is configured to retain drive bar 391 and mandrel 392 therein. Further, a biasing member, e.g., spring 354, may be disposed between proximal wall 352 of cartridge 350 and mandrel 392 to bias drive bar 391 toward a distal position, e.g., to bias jaw members 110, 120 toward a spaced-apart position. Thus, when lever 341 is released, cartridge 350, mandrel 392 and drive bar 391 are translated distally along longitudinal axis "X-X," under the bias of spring 354, to return jaw members 110, 120 to the spaced-apart position.

Figure 12:
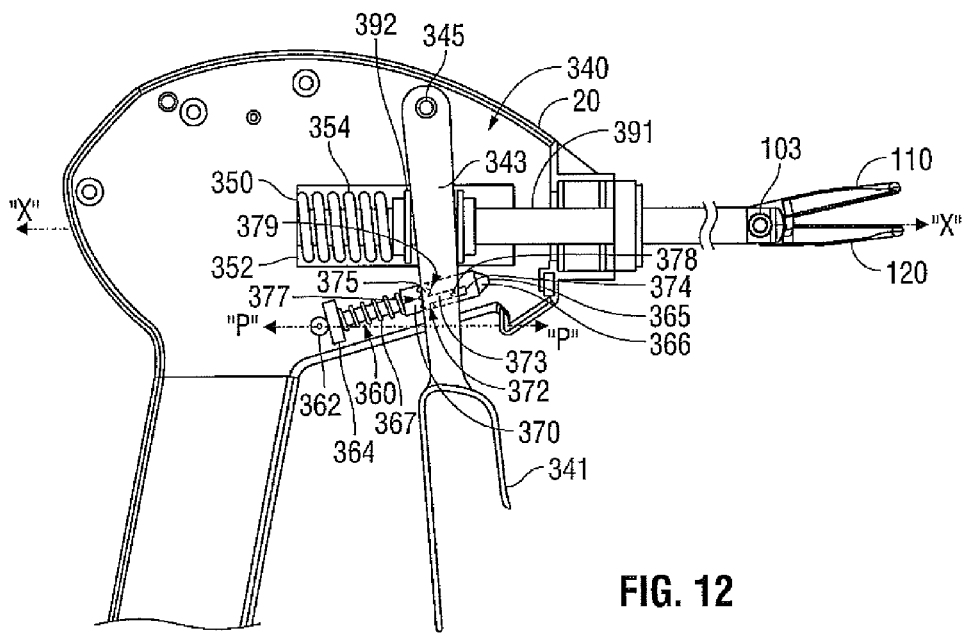
FIG. 12 is a side, cross-sectional view of yet another embodiment of a latch mechanism configured for use with the forceps of FIG. 1A, wherein the lever is disposed in an initial position.
Figure 13:
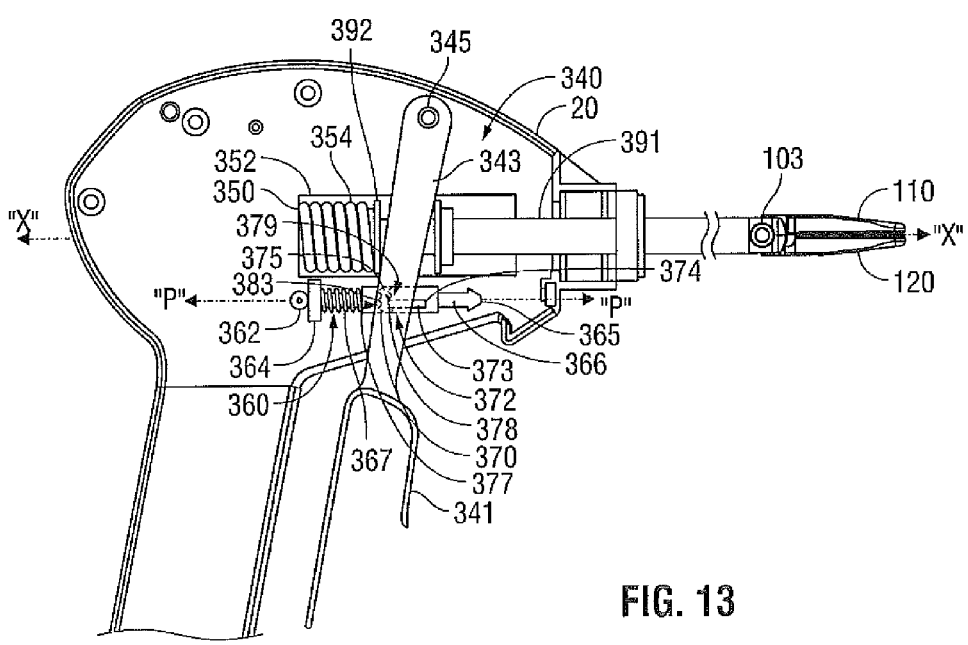
FIG. 13 is a side, cross-sectional view of the forceps of FIG. 12, wherein the lever is disposed in the actuated position and wherein the latch mechanism is disposed in the latched condition.
Figure 14:
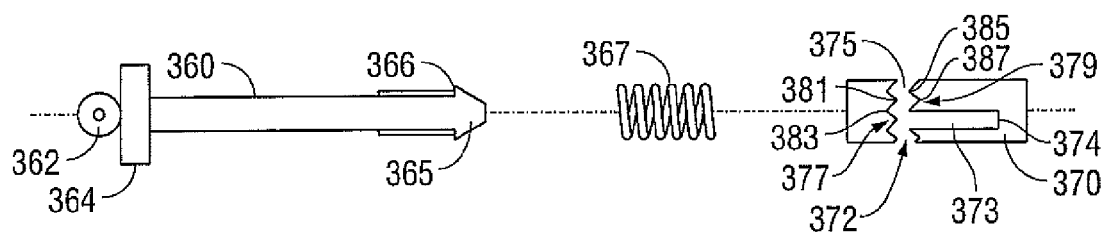
FIG. 14 is a side view of the post assembly of the latch mechanism of the forceps of FIG. 12 shown with parts separated.
Figure 15:
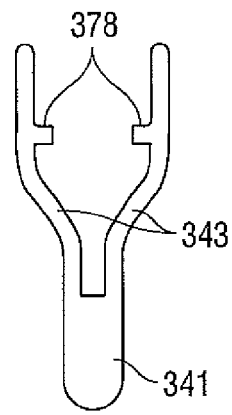
FIG. 15 is a front view of the lever of the latch assembly of FIG. 12.

With continued reference to FIGS. 12-15, lever latch mechanism 340 further includes a post 360 pivotably coupled to housing 20 at proximal end 362 thereof. Post 360 includes a proximal shoulder 364 disposed at proximal end 362 thereof and a distal snap feature 366 disposed at a distal end 365 thereof. As best shown in FIG. 15, a biasing member, e.g., a spring 367, is positionable about post 360 adjacent proximal shoulder 364. A sleeve 370 having a track 372 defined therein on an outer periphery thereof is slidably and rotatably positionable about post 360. More particularly, sleeve 370 is configured to slide over distal end 365 of post 360 such that sleeve 370 is snap-fittingly retained thereon. In other words, once sleeve is slid over post 360, snap-fit feature 366 inhibits sleeve 370 from being removed from post 360. Other mechanisms (not shown) that are configured to retain sleeve 370 on post 360 while allowing sleeve 370 to translate and rotate relative to post 360 may also be provided. As assembled, as shown in FIGS. 12 and 13, spring 367 is interdisposed between proximal shoulder 364 of post 360 and sleeve 370, biasing sleeve 370 toward distal end 365 of post 360.

As mentioned above, sleeve 370 includes a track 372 defined therein. Track 372 is similar to track 160 defined within sleeve 150 of lever latch assembly 140 (see FIGS.

2A-7) and extends annularly about sleeve 370. More specifically, track 372 includes one or more longitudinal segments 373 and one or more annular segments 375. The proximal and distal surfaces 377, 379, respectively, of annular segments 375 of track 372 define triangle-wave-shaped configurations that are offset relative to one another.

As best shown in FIG. 15, lever 341 includes a pair of opposed stop members 378 extending inwardly from flanges 343. Stop members 378 are configured to engage track 372 of sleeve 370 and to translate along track 372 of sleeve 370. Due to the triangle-wave-shaped configuration of track 372, stop members 378 also urge sleeve 370 to rotate about post 360 upon translation of stop members 378 along track 372, as will be described in greater detail below.

Turning now to FIGS. 12-13, in conjunction with FIG. 14, the use and operation of lever latch assembly 340 will be described. Initially, as shown in FIG. 12, lever 341 is disposed in the initial position, jaw members 110, 120 are disposed in the spaced-apart position, and stop members 378 of lever 341 are disposed at distal ends 374 of longitudinal segments 373 of track 372 of sleeve 370. In this initial position, post 360 is angled upwardly off of post axis "P-P" toward drive bar 391 and sleeve 370 is biased toward distal end 365 of post 360 by spring 367.

In order to move jaw members 110, 120 to the approximated position, e.g., to grasp tissue therebetween, lever 341 is pulled proximally from the initial position toward the actuated position. As lever 341 is pulled proximally, cartridge 350 and drive bar 391 are likewise translated proximally against the bias of spring 354 to pivot jaw members 110, 120 relative to one another from the spaced-apart position toward the approximated position. At the same time, stop members 378 of lever 341 are translated proximally along longitudinal segments 373 of track 372 of sleeve 370. Further, as stop members 378 are translated along track 372 of sleeve 370, i.e., as lever 373 is translated proximally, post 360 is pivoted downwardly about proximal end 362 thereof toward post axis "P-P."

As in the previous embodiments, lever 341 is moved further proximally until stop members 378 have translated proximally completely through longitudinal segments 373 of track 372 and into abutment with proximal surface 377 of track 372. This position corresponds to the over-actuated position of lever 341. Upon contact of stop members 378 with the proximal surface 377 of track 372, stop members 378 are urged against the triangle-wave-shaped proximal surface 377 of track 372, causing sleeve 370 to rotate about post 360, moving stop members 378 along track 372 from the peaks 381 of proximal surface 377 of track 372 to the valleys 383 thereof (see FIG. 14).

Once lever 341 has been moved to the over-actuated position, lever 341 may be released such that lever 341 and stop members 378 are translated distally relative to track 372 under the bias of spring 367. Eventually, stop members 378 are translated distally into engagement with distal surface 379 of track 372 under the bias of spring 367, while cartridge 350 and drive bar 391 are returned distally under the bias of spring 354. However, upon engagement between stop members 378 and distal surface 379 of track 372, further distal translation of stop members 378, lever 341, cartridge 350 and drive bar 391 is inhibited. More specifically, as stop members 378 are translated distally into engagement with distal surface 379 of track 372, stop members 378 urge sleeve 370 to rotate about post 360 such that stop members 378 are translated from the peaks 385 of distal surface 379 to the valleys 387 thereof (see FIG. 14). Spring 367 biases stop members 378 into valleys 387 of distal surface 379 of track 372, inhibiting further distal translation of lever 341, mandrel 392 and drive bar 391. This position, as shown in FIG. 13, corresponds to the latched condition of lever latch assembly 340, wherein lever 341 is latched in the actuated position and wherein jaw members 110, 120 are latched in the approximated position.

Similarly as described above with reference to lever latch assemblies 140 and 240 (see FIGS. 2A-7 and 8-11, respectively), to unlatch lever latch assembly 340, lever 341 is pulled proximally from the actuated position to the over-actuated position to translate stop members 378 proximally into engagement with proximal surface 377 of track 372. Upon contact with the triangle-wave-shaped proximal surface 377 of track 372, stop members 378 urge sleeve 370 to rotate about post 360 such that stop members 378 are moved to the valleys 383 of proximal surface 377 of track 372.

Thereafter, lever 341 may be released, allowing lever 341, cartridge 350 and drive bar 391 to return distally, thus allowing jaw members 110, 120 to move back toward the spaced-apart position. At the same time, stop members 378 are translated distally along track 372, eventually contacting distal surface 379 of track 372 and urging sleeve 370 to rotate about post 360 until stop members 378 are once again aligned with longitudinal segments 373 of track 372. Once this position is achieved, lever 341 is permitted to translate distally back to the initial position as stop members 378 are translated distally through longitudinal segments 373 of track 372 to distal ends 374 thereof. Likewise, cartridge 350 and drive bar 391 are return distally under the bias of spring 354, urging jaw members 110, 120 to pivot relative to one another back to the spaced-apart position.

Figure 16:
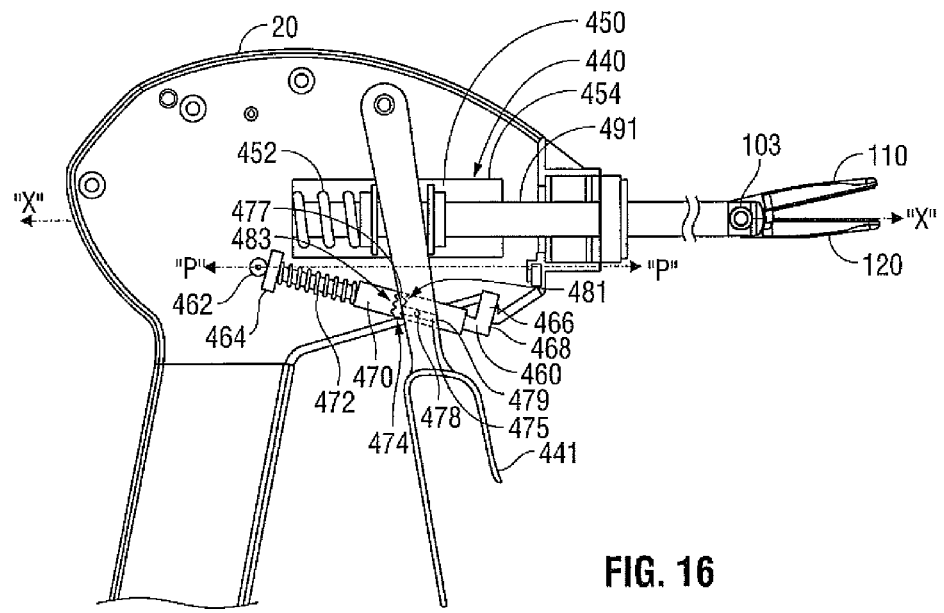
FIG. 16 is a side, cross-sectional view of still another embodiment of a latch mechanism configured for use with the forceps of FIG. 1A, wherein the latch mechanism is disposed in an unlatched condition.
Figure 17:
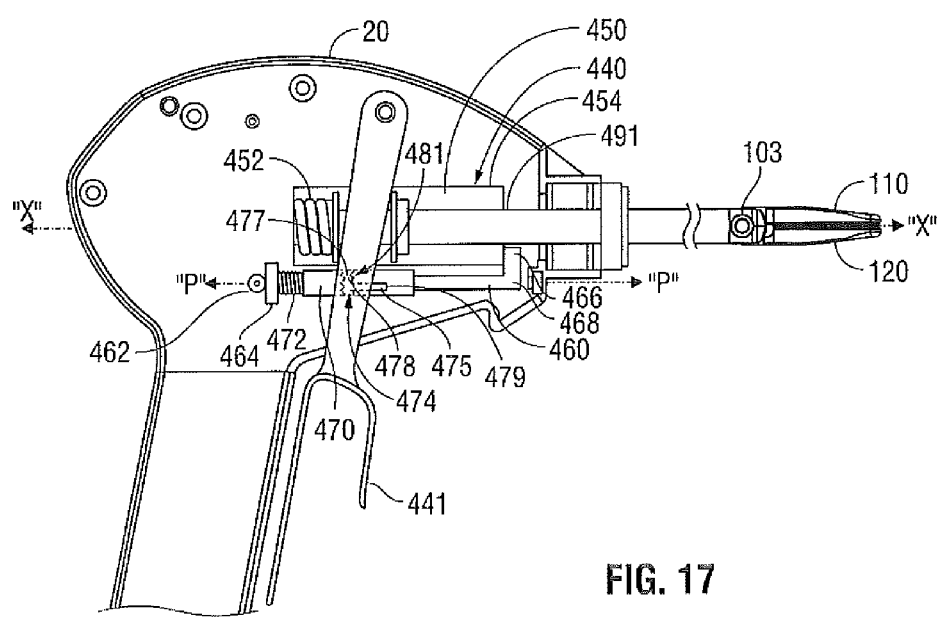
FIG. 17 is a side, cross-sectional view of the latch mechanism of FIG. 16, wherein the latch mechanism is disposed in a latched condition.

With reference now to FIGS. 16-17, yet another embodiment of a lever latch assembly is shown. Lever latch assembly 440 is substantially similar to lever latch assembly 340 (FIGS. 12-15) and includes a post 460 pivotably coupled to housing 20 at proximal end 462 thereof. Post 460 further includes a proximal shoulder 464 disposed at proximal end 462 thereof and an interference member 466 disposed at a distal end 468 thereof. A spring 472 is positionable about post 460 adjacent proximal shoulder 464. A sleeve 470 including a track 474 defined therein on an outer periphery thereof is slidably and rotatably positionable about post 460 such that spring 472 is interdisposed between proximal shoulder 464 of post 460 and sleeve 470. Sleeve 470 is substantially similar to sleeve 370 of lever latch assembly 340 (see FIGS. 12-15) and includes a track 474 having one or more longitudinal segments 475 and one or more annular segments 477 extending annularly about sleeve 470 in alternating relation relative to one another. As described above in previous embodiments, stop members 478 of lever 441 are engaged within track 474 of sleeve 470 and are translatable therealong. Track 474 of sleeve 470 is substantially similar to the tracks of lever latch assemblies 140, 240, 340, described above.

Initially, as shown in FIG. 16, lever 441 is disposed in the initial position, jaw members 110, 120 are disposed in the spaced-apart position, and stop members 478 of lever 441 are disposed at distal ends 479 of longitudinal segments 475 of track 474 of sleeve 470. Further, in this initial position, post 460 is angled downwardly relative to post axis "P-P."

In order to move jaw members 110, 120 to the approximated position, lever 441 is pulled proximally from the initial position toward the actuated position, translating cartridge 450 and drive bar 491 proximally against the bias of spring 452 and pivoting jaw members 110, 120 toward the approximated position. At the same time, stop members 478 of lever 441 are translated proximally along longitudinal segments 475 of track 474 of sleeve 470. As stop members 478 are translated along longitudinal segments 475 of track 472 of sleeve 470, post 460 is pivoted upwardly into alignment with post axis "P-P." In this position, interference member 466, which is disposed at distal end 468 of post 460, is moved into position adjacent a distal end 454 of cartridge 450. More particularly, in this position, interference member 466 is disposed between housing 20 and cartridge 450 to inhibit distal translation of cartridge 450 along longitudinal axis "X-X."

As in the previous embodiments, lever 441 is moved proximally until stop members 478 have been translated proximally completely through longitudinal segments 475 of track 474 and into abutment with triangle-wave-shaped proximal surface 483 of track 474 to rotate sleeve 470 about post 460, as discussed above. Thereafter, upon release of lever 441, stop members 478 are translated distally relative to track 474 into engagement with distal surface 481 of track 474. With stop members 478 engaged within distal surface 481 of track 474 of sleeve 470, post 460 is retained in position relative to post axis "P-P," e.g., in alignment with post axis "P-P." As mentioned above, in this position, interference member 466 is disposed between housing 20 and cartridge 450, inhibiting cartridge 450 and, thus, drive bar 491 from returning distally, thereby latching jaw members 110, 120 in the approximated position. As can be appreciated, when jaw members 110, 120 are latched in the approximated position, lever 441 is latched in the actuated position.

In order to unlatch lever latch assembly 440, lever 441 is pulled proximally from the actuated position to the over-actuated position such that stop members 478 are translated proximally from distal surface 481 of track 474, into engagement with proximal surface 483 of track 474. The triangle-wave-shaped configuration of proximal surface 483 of track 474 urges sleeve 470 to rotate about post 460 upon contact with stop members 478 such that stop members 478 are moved into alignment with longitudinal segments 475 of track 474. With stop members 478 aligned with longitudinal segments 475 of track 474, lever 441 is permitted, upon release thereof, to translate from the actuated position back to the initial position as stop members 478 are translated distally through longitudinal segments 475 of track 474. At the same time, post 460 is pivoted about proximal end 462 thereof downwardly relative to post axis "P-P," disengaging interference member 466 from between cartridge 450 and housing 20. With interference member 466 no longer inhibiting cartridge 450 and drive bar 491 from returning distally, spring 452 urges cartridge 450 and drive bar 491 distally such that jaw members 110, 120 are returned to the spaced-apart position.

With reference now to FIGS. 18-20B, still another embodiment of a lever latch assembly is shown configured for use with forceps 10. Lever latch assembly 540 includes a lever 541 having a pair of flanges 543 disposed on either side of drive bar 591 and between proximal and distal rims 593, 594, respectively, of mandrel 592, such that moving lever 541 between the initial position and the actuated position translates drive bar 591 longitudinally along longitudinal axis "X-X" to move jaw members 110, 120 between the spaced-apart position and the approximated position. Further, mandrel 592 and drive bar 591 are disposed within a cartridge 550. Cartridge 550 is disposed within housing 20 and is positioned about longitudinal axis "X-X." Cartridge 550 is configured to retain drive bar 591 and mandrel 592 therein and includes a spring 552 disposed between proximal wall 554 of cartridge 550 and proximal rim 593 of mandrel 592 to bias drive bar 591 distally, e.g., to bias jaw members 110, 120 toward the spaced-apart position.

Continuing with reference to FIGS. 18-20A, lever latch mechanism 540 further includes a post 560 pivotably coupled to housing 20 at proximal end 563 thereof. Post 560 includes a proximal shoulder 562 disposed at proximal end 563 thereof and a distal snap feature 566 disposed at a distal end 565 thereof. A sleeve 570 including a track 572 defined on an outer periphery thereof and an annular recess 580 defined therein is slidably and rotatably positionable about post 560. An "L"-shaped spring 576 is disposed about and engaged to post 560 at proximal end 563 thereof and extends distally therefrom. "L"-shaped spring 576 includes a stop member 578 disposed at the free end thereof that extends downwardly into engagement with track 572 of sleeve 570.

Track 572 of sleeve 570 is similar to track 572 defined within sleeve 570 of lever latch assembly 140 (see FIGS. 2A-7), except that longitudinal segments 573 of track 572 extend proximally along sleeve 570 from annular segments 574 of track 572. As mentioned above, stop member 578 of "L"-shaped spring 576 is engaged within track 572 and is translatable along track 572. Lever 541, on the other hand, includes a pair of protrusions 542 extending inwardly from flanges 543. Protrusions 542 of lever 541 are engaged within annular recess 580 of sleeve 570 such that, as lever 541 is moved between the initial position and the actuated position, sleeve 570 is translated along post 560. At the same time, post 560 is pivoted relative to post axis "P-P" about proximal end 563 of post 560 as lever 541 is moved between the initial position and the actuated position. As will be described in greater detail below, as lever 451 is moved between the initial position and the actuated position to pivot post 560 and translate sleeve 570 along post 560, stop member 578 of "L"-shaped spring 576 is translated along track 572 defined within sleeve 570 to latch and unlatch lever latch assembly 540.

Figure 18:
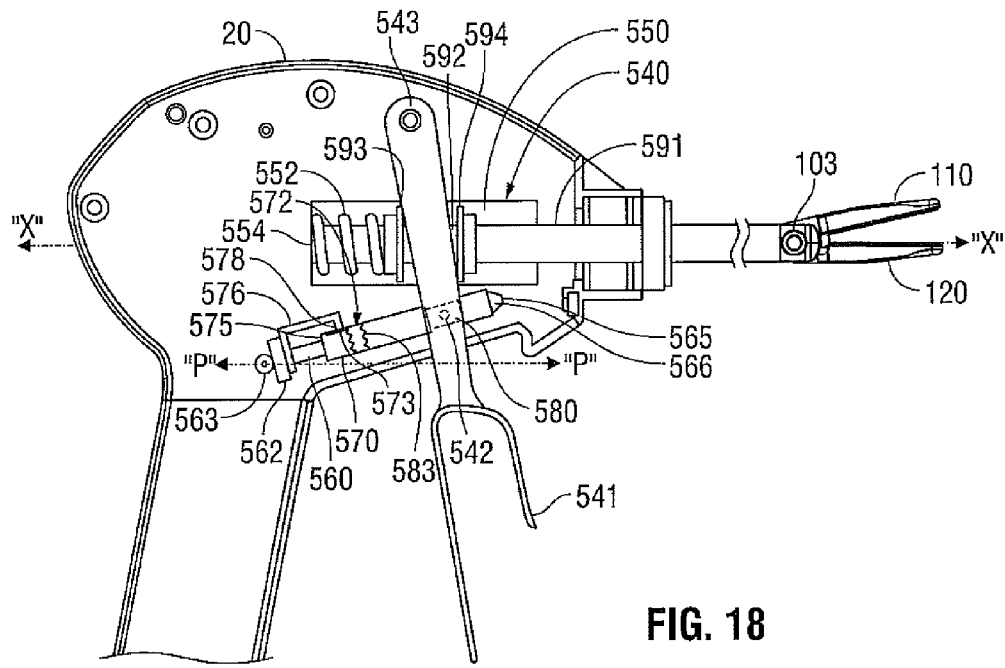
FIG. 18 is a side, cross-sectional view of still yet another embodiment of a latch mechanism configured for use with the forceps of FIG. 1A, wherein the latch mechanism is disposed in an unlatched condition.

With continued reference to FIGS. 18-20A, the use and operation of lever latch assembly 540 will be described. Initially, as shown in FIG. 18, lever 541 is disposed in the initial position, jaw members 110, 120 are disposed in the spaced-apart position, stop member 578 of "L"-shaped spring 576 is disposed at proximal end 575 of longitudinal segment 573 of track 572, and protrusions 542 of lever 541 retain sleeve 570 toward a distal end 565 of post 560. Further, in this initial position, post 560 is angled upwardly relative to post axis "P-P" toward drive bar 591, as shown in FIG. 18.

In order to move jaw members 110, 120 to the approximated position, as in the previous embodiments, lever 541 is pulled proximally from the initial position toward the actuated position, translating cartridge 550 and drive bar 591 proximally against the bias of spring 552 to pivot jaw members 110, 120 toward the approximated position. At the same time, protrusions 542 of lever 541 urge sleeve 570 proximally along post 560 and effect pivoting of post 560 downwardly toward post axis "P-P." Further, upon movement of lever 541 toward the actuated position, stop member 578 of "L"-shaped spring 576 is moved distally relative to sleeve 570 along longitudinal segment 573 of track 572.

Lever 541 is moved further proximally to the over-actuated position to translate sleeve 570 further distally relative to post 560 such that stop member 578 of "L"-shaped spring 576 is translated completely through longitudinal segment 573 of track 572 and into engagement with distal surface 583 of track 572. As stop member 578 is urged against the triangle-wave-shaped distal surface 583 of track 572, sleeve 570 is rotated above post 560 and relative to "L"-shaped spring 576 to engage stop member 578 within distal surface 583 of track 572.

Figure 19:
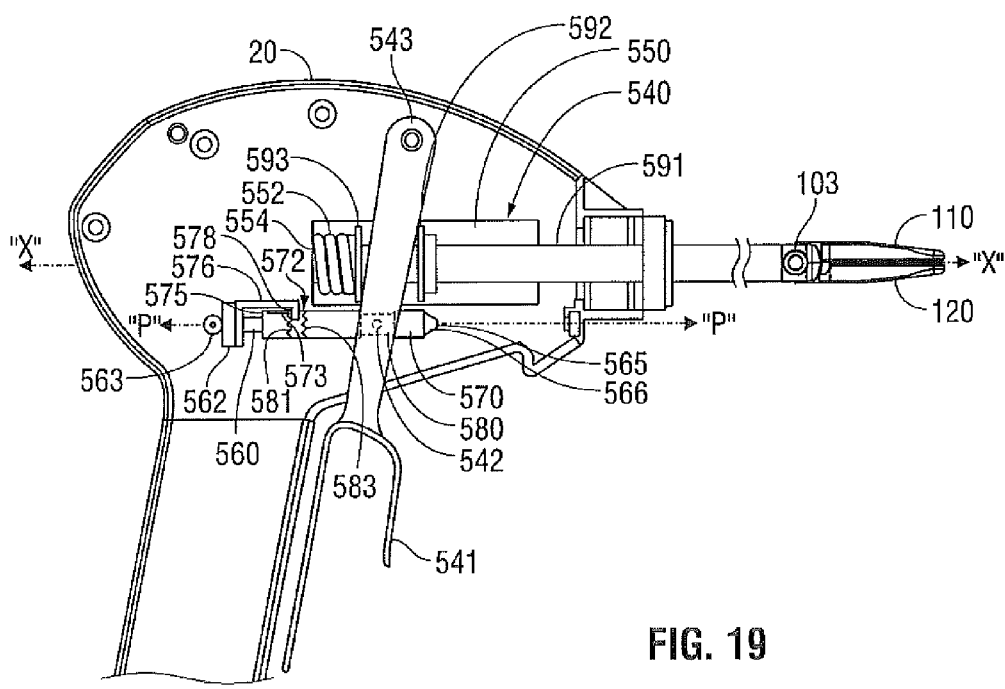
FIG. 19 is a side, cross-sectional view of the latch mechanism of FIG. 18, wherein the latch mechanism is disposed in a latched condition.

Thereafter, upon release of lever 541, stop member 578 is translated proximally relative to track 572, under the bias of "L"-shaped spring 576, into engagement with proximal surface 581 of track 572. Stop member 578 is retained in engagement with the triangle-wave-shaped proximal surface 581 of track 572 under the bias of "L"-shaped spring 576, inhibiting lever 541, sleeve 570, cartridge 550 and drive bar 591 from returning distally. This latched condition, as shown in FIG. 19, corresponds to the actuated position of lever 541 and, thus, the approximated position of jaw members 110, 120. In the actuated position, as shown in FIG. 19, post 560 is substantially aligned with post axis "P-P."

Lever latch assembly 540 is unlatched similarly to lever latch assemblies 140, 240, 340, and 440, discussed above. More specifically, to unlatch lever latch assembly 540, lever 541 is pulled proximally from the actuated position to the over-actuated position such that protrusions 542 of lever 541 urge sleeve 570 proximally along post 560. As a result, sleeve 570 is moved distally relative to stop member 578 such that stop member 578 is translated from proximal surface 581 of track 572 into engagement with distal surface 583 of track 572. The triangle-wave-shaped configuration of distal surface 583 of track 572 urges sleeve 570 to rotate about post 560 upon contact with stop member 578.

Thereafter, upon release of lever 541, cartridge 550 and drive bar 591 are returned distally under the bias of spring 552 such that jaw members 110, 120 are moved back toward the spaced-apart position. At the same time, lever 541 is returned distally, thereby translating sleeve 570 distally along post 560, causing post 560 to pivot upwardly relative to post axis "P-P" toward drive bar 591. Further, due to the distal translation of sleeve 570 relative to "L"-shaped spring 576, stop member 578 is translated along track 572 into engagement with triangle-wave-shaped distal surface 583 of track 572. More particularly, stop member 578 is urged into engagement with distal surface 583 of sleeve 570 such that sleeve 570 is rotated about post 560 until stop member 578 is moved into alignment with longitudinal segment 573 of track 572. With stop member 578 aligned with longitudinal segment 573 of track 572, lever 541 is permitted to translate distally back to the initial position as stop member 578 is translated proximally through longitudinal segment 573 of track 572. At the same time, sleeve 570, cartridge 550 and drive bar 591 are returned distally and jaw members 110, 120 are returned to the spaced-apart position.

Figure 20A:
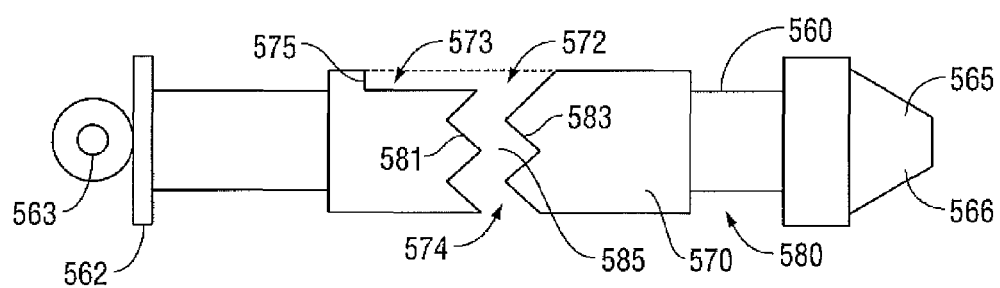
FIG. 20A is a greatly-enlarged, side view of the latch mechanism of FIG. 18.
Figure 20B:
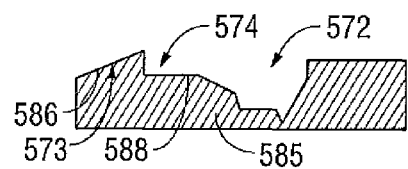
FIG. 20B is a transverse-cross sectional view of the latch mechanism of FIG. 20A represented linearly.

Turning now to FIGS. 20A and 2013, post 560 is shown including sleeve 570 disposed thereabout. As discussed in detail above, track 572 defined within sleeve 570 includes one or more annular triangle-wave-shaped segments 574 and one or more longitudinal segments 573 extending proximally from annular segment(s) 574. Track 572 may further include a contoured floor 585 correspondingly configured relative to the annular and longitudinal segments 574, 573, respectively, of track 572. More specifically stop member 578 of "L"-shaped spring 576 (FIGS. 18-19) may be configured to not only translate longitudinally and rotationally relative to track 572, but may further be configured to translate radially, e.g., inwardly and outwardly, with respect to track 572, as a function of the contoured floor 585 of track 572. Such a feature provides for three-dimensional translation of stop member 578 (FIGS. 18-19) along track 572 to increase the engagement and positioning of stop member 578 (FIGS. 18-19) relative to sleeve 570. For example, as stop member 578 (FIGS. 18-19) is translated distally along longitudinal segment 573 of track 572, stop member 578 (FIGS. 18-19) may likewise be translated along an upwardly-angled portion 586 of contoured floor 585 of track 572. Stop member 578 (FIGS. 18-19) may then drop-off into a lower-disposed portion 588 of floor 585 upon positioning within annular segment 574 of track 572. As can be appreciated, and as shown in FIG. 206, floor 585 of track 572 may define a plurality of other varying depth and/or angled portions such that stop member 578 (FIGS. 18-19) may be translated through these various portions of floor 585 as stop member 578 (FIGS. 18-19) is translated from longitudinal segment 573, proximal and distal surfaces 581, 583, respectively, of annular segment 574, and back to longitudinal segment 573 of track 572. Other configurations of track 572 may also be provided. Additionally, any of the tracks of lever latch assemblies 140, 240, 340, 440 discussed above may include similarly-configured contoured floors to define a three-dimensional configuration.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A surgical instrument, comprising:
   an end effector assembly including a pair of jaw members pivotably coupled to one another, at least one of the jaw members moveable relative to the other between a spaced-apart position and an approximated position for grasping tissue therebetween;
   a drive bar defining a longitudinal axis, the drive bar longitudinally translatable between a distal position and a proximal position for moving the jaw members between the spaced-apart position and the approximated position; and
   a latch mechanism including:
      a lever moveable between an initial position and an actuated position for translating the drive bar between the distal position and the proximal position, the lever further moveable to an over-actuated position;
      a sleeve co-axially disposed about the drive bar, the sleeve including a track having a substantially radial segment that extends annularly around the sleeve in a radial direction and a substantially longitudinal segment that extends from the substantially radial segment longitudinally along the sleeve in an axial direction; and
      a rotatable collar interdisposed between the sleeve and the drive bar, the rotatable collar including a stop member extending radially outwardly from an outer periphery of the rotatable collar, the stop member engaged within the track,
   wherein, movement of the lever between the initial position and the actuated position effects movement of the stop member within the substantially longitudinal segment of the track in the axial direction,
   wherein, when the at least one stop member is disposed within the substantially longitudinal segment, movement of the lever from the actuated position to the over-actuated position effects movement of the stop member in both the axial direction and the radial direction from the substantially longitudinal segment to the substantially radial segment to lock the lever in the actuated position, and
   wherein, when the stop member is disposed within the substantially radial segment, movement of the lever from the actuated position to the over-actuated position effects movement of the stop member in both the axial direction and the radial direction from the substantially radial segment to the substantially longitudinal segment to unlock the lever from the actuated position.

2. The surgical instrument according to claim 1, wherein the substantially radial segment of the track defines at least one engagement feature configured to receive the stop member to lock the lever in the actuated position.

3. The surgical instrument according to claim 1, wherein the track includes a plurality of alternating substantially longitudinal segments and substantially radial segments, the substantially longitudinal segments extending distally along the sleeve relative to the substantially radial segments.

4. The surgical instrument according to claim 1, further comprising a biasing member annularly disposed between the drive bar and the sleeve, the biasing member configured to bias the rotatable collar distally relative to the sleeve.

* * * * *